United States Patent
Abbott et al.

(10) Patent No.: US 11,094,221 B2
(45) Date of Patent: Aug. 17, 2021

(54) VISUAL GUIDANCE SYSTEM AND METHOD FOR POSING A PHYSICAL OBJECT IN THREE DIMENSIONAL SPACE

(71) Applicant: University of Utah Research Foundation, Salt Lake City, UT (US)

(72) Inventors: Jacob J Abbott, Salt Lake City, UT (US); David E. Usevitch, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 16/530,559

(22) Filed: Aug. 2, 2019

(65) Prior Publication Data

US 2020/0035122 A1 Jan. 30, 2020

Related U.S. Application Data

(63) Continuation-in-part of application No. 16/448,967, filed on Jun. 21, 2019, now abandoned.
(Continued)

(51) Int. Cl.
  *G09B 19/00* (2006.01)
  *A61B 34/00* (2016.01)
  (Continued)

(52) U.S. Cl.
  CPC ............ *G09B 19/003* (2013.01); *A61B 34/25* (2016.02); *G06T 15/10* (2013.01); *G01P 13/00* (2013.01)

(58) Field of Classification Search
  CPC ....... G09B 19/003; A61B 34/25; G06T 15/10; G01P 13/00
  See application file for complete search history.

(56) References Cited

U.S. PATENT DOCUMENTS

| 6,875,179 B2 | 4/2005 | Ferguson et al. |
| 7,067,797 B1 | 6/2006 | Mitchell et al. |
| (Continued) | | |

FOREIGN PATENT DOCUMENTS

| WO | WO 2000/064367 | 4/2000 |
| WO | WO 2019/103954 A1 | 5/2019 |

OTHER PUBLICATIONS

Mendes, A Survey on 3D Virtual Object Manipulation From the Desktop to Immersive Virtual Environments, Computer Graphics forum, vol. 38 (2019), No. 1 pp. 21-5, paper published on Apr. 2018. (Year: 2018).*

(Continued)

*Primary Examiner* — Phuc N Doan
(74) *Attorney, Agent, or Firm* — Thorpe North & Western, LLP

(57) ABSTRACT

A method and system of visually communicating navigation instructions can use translational and rotational arrow cues (TRAC) defined in an object-centric frame while displaying a single principal view that approximates the human's egocentric view of the actual object. A visual guidance system and method can be used to pose a physical object within three-dimensional (3D) space. Received pose data (402) indicates a current position and orientation of a physical object within 3D space, such that the pose data can provide a view of the physical object used to generate a virtual view of the physical object in 3D space. At least two of six degrees of freedom (6DoF) error can be calculated (404) based on a difference between the current position of the physical object and a target pose of the physical object. The 6DoF error can include a three degrees of freedom (3DoF) position error and a 3DoF orientation error which can be used to determine a translation direction and a rotation direction to move the physical object to align a pose of the physical object with the target pose of the physical (Continued)

object within a tolerance. One of both of a translation cue and a rotation cue can be output (408) to indicate a translation direction or rotation direction to move the physical object in alignment with the target pose.

22 Claims, 10 Drawing Sheets

Related U.S. Application Data

(60) Provisional application No. 62/688,277, filed on Jun. 21, 2018.

(51) Int. Cl.
  *G06T 15/10* (2011.01)
  *G01P 13/00* (2006.01)

(56) References Cited

U.S. PATENT DOCUMENTS

| | | | | |
|---|---|---|---|---|
| 8,335,590 | B2* | 12/2012 | Costa | A61B 34/37 |
| | | | | 700/259 |
| 9,155,675 | B2 | 10/2015 | Ye | |
| 9,314,305 | B2 | 4/2016 | Jenkins et al. | |
| 9,554,812 | B2 | 1/2017 | Inkpen et al. | |
| 9,782,229 | B2 | 10/2017 | Crawford et al. | |
| 9,901,411 | B2 | 2/2018 | Gombert et al. | |
| 10,089,965 | B1* | 10/2018 | Ward | G09G 3/003 |
| 10,123,766 | B2 | 11/2018 | Mourad et al. | |
| 10,139,920 | B2 | 11/2018 | Isaacs et al. | |
| 10,198,874 | B2 | 2/2019 | Dearman et al. | |
| 10,299,883 | B2 | 5/2019 | Kilroy et al. | |
| 10,664,993 | B1* | 5/2020 | Reddy | G06T 7/73 |
| 2005/0020909 | A1 | 1/2005 | Moctezuma De La Barrera et al. | |
| 2009/0293012 | A1* | 11/2009 | Alter | G06F 3/0346 |
| | | | | 715/810 |
| 2010/0102980 | A1* | 4/2010 | Troy | G05B 19/042 |
| | | | | 340/686.6 |
| 2013/0093756 | A1* | 4/2013 | Davidson | G06F 3/04845 |
| | | | | 345/419 |
| 2014/0200440 | A1 | 7/2014 | Iannotti et al. | |
| 2016/0183841 | A1 | 6/2016 | Duindam et al. | |
| 2016/0259424 | A1* | 9/2016 | Nataneli | G06F 3/03543 |
| 2017/0080574 | A1 | 3/2017 | Kuroda et al. | |
| 2017/0165008 | A1 | 6/2017 | Finley | |
| 2017/0287221 | A1 | 10/2017 | Ghaly et al. | |
| 2019/0018567 | A1* | 1/2019 | Murphy | G06F 3/012 |
| 2019/0123598 | A1 | 4/2019 | Patmore et al. | |
| 2019/0192232 | A1* | 6/2019 | Altmann | A61B 5/743 |
| 2020/0138518 | A1* | 5/2020 | Lang | A61B 5/05 |

OTHER PUBLICATIONS

Bhattacharya, Automatic generation of augmented reality guided assembly instructions using expert demonstration, PhD. These, Iowa State University Ames, Iowa (Year: 2016).*
Adams et al.; "Computer-Assisted Surgery." IEEE Computer Graphics and Applications; 1990; vol. 10, Issue 3; pp. 43-51.
Dagnino et al.; "Navigation System for Robot-Assisted Intra-Articular Lower-Limb Fracture Surgery." International Journal of Computer Assisted Radiology and Surgery; vol. 11, Issue 10; 2016; pp. 1831-1843.
Galloway et al.: "Interactive Image-Guided Neurosurgery." IEEE Transactions on Biomedical Engineering; Dec. 1992; vol. 39, Issue 12; pp. 1226-1231.
Jacob et al.; "Integrality and Separability of Input Devices." ACM Transactions on Computer-Human Interaction (TOCHI), 1994; vol. 1, Issue 1; pp. 3-26.
Labadie et al.; "Image-Guided Surgery." Fundamentals and Clinical Applications in Otolaryngology; Plural Publishing Inc.
Parsons.; "Inability to Reason About an Object's Orientation Using an Axis and Angle of Rotation." Journal of Experimental Psychology. Human Perception and Performance; 1995; vol. 21, Issue 6; pp. 1259-1277.
Sen et al.; "System Integration and Preliminary In-Vivo Experiments of a Robot for Ultrasound Guidance and Monitoring during Radiotherapy." In Proceedings of the IEEE 2015 International Conference on Advanced Robotics (ICAR), 2015; pp. 53-59.
Sun et al.; "Computer-Guided Ultrasound Probe Realignment by Optical Tracking." In Proceedings of the IEEE $10^{th}$ International Symposium on Biomedical Imaging (ISBI), 2013; pp. 21-24.
Traub et al.; "Towards a Hybrid Navigation Interface: Comparison of a Slice Based Navigation System with In-Situ Visualization" In International Workshop on Medical Imaging and Virtual Reality; Springer, 2006; pp. 179-186.
Ware et al.; "Frames of Reference in Virtual Object Rotation." In Proceedings of the $1^{st}$ Symposium on Applied Perception in Graphics and Visualization; ACM, 2004; pp. 135-141.

* cited by examiner (a) AA Method: (left) Session A, pure orientation; (right) Session B, pure translation.

(b) SA Method: (left) Session A, pure orientation; (right) Session B, pure translation.

VISUAL GUIDANCE SYSTEM AND METHOD FOR POSING A PHYSICAL OBJECT IN THREE DIMENSIONAL SPACE

RELATED APPLICATION

This application is a continuation-in-part of U.S. application Ser. No. 16/448,967, filed Jun. 21, 2019, which claims priority to U.S. Provisional Application No. 62/688,277, filed Jun. 21, 2018, which are each incorporated herein by reference.

GOVERNMENT INTEREST

This invention was made with government support under grant no. DC013168 awarded by the National Institutes of Health. The government has certain rights in the invention.

BACKGROUND

Image guided tasks can be performed by a user who manually positions an object in space with six degrees-of-freedom (6-DoF). Displaying a current and desired pose of the object on a 2D display (e.g., a computer monitor) may be straightforward, however, providing guidance to accurately and rapidly navigate the object in 6-DoF can be challenging. One technique for guiding a user to manually position an object in space uses a triplanar display. A triplanar display can simultaneously show three distinct orthogonal viewpoints of a workspace. When working with the human body, the sagittal, coronal, and axial planes may be used as references for view placement, and the arrangement of the three orthogonal views on the triplanar display can differ widely, with no universally accepted or consistent definition. Although the triplanar display may be commonly used, the triplanar display can be quite unintuitive, particularly for those without practice, such that performing an accurate 6-DoF alignment task can take a relatively large amount of time. Accordingly, an improved technique for guiding a user to manually position an object in space is needed.

SUMMARY

Technologies are described for a visual guidance system and method used to pose a physical object within three-dimensional (3D) space. In one example, pose data can be received from a motion tracking system. The pose data indicates a current position and orientation of a physical object within 3D space, such that the pose data can provide a view of the physical object used to generate a virtual view of the physical object in 3D space. At least two of six degrees of freedom (6DoF) error can be calculated based on a difference between the current position of the physical object and a target pose of the physical object. The 6DoF error can include a three degrees of freedom (3DoF) position error and a 3DoF orientation error which can be used to determine a translation direction and a rotation direction to move the physical object to align a pose of the physical object with the target pose of the physical object within a tolerance.

A virtual representation of the current position and orientation of the physical object can be output to a display as a virtual pose indicated by the pose data. In one example, a virtual object representing the physical object and the current position and orientation of the physical object can be output to the display. In another example, a coordinate frame can be output to the display, where the coordinate frame represents a current position and orientation of the physical object in the 3D space. In yet another example, the coordinate frame can be attached to the virtual object output to a display to indicate a location of the virtual object in the 3D space.

One or more visual cues can be output to the display to indicate a direction to move the physical object that aligns the physical object with a target pose. For example, a translation cue can be output to the display to indicate a translation direction to move the physical object along a translation axis of the physical object based on the 3DoF position error in order to align a position of the physical object with the target pose of the physical object within a tolerance. A rotation cue can be output to the display to indicate a rotation direction to move the physical object along a rotation axis of the physical object based on the 3DoF orientation error in order to align an orientation of the physical object with the target pose of the physical object within the tolerance. In one example, a visual cue output to the display can be selected based on a 3DoF error linked to the visual cue that is greater than other 3DoF errors linked to other visual cues.

Visually communicating navigation instructions using translational and rotational cues defined in an object-centric frame while displaying a single principal view that approximates a user's egocentric view of the physical object can be useful in performing tasks to manually position an object in space, such as image-guided surgery, as well as other tasks in which a user manually positions and orients a physical object in space in some predetermined position with some predetermined accuracy.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

Figure 1:
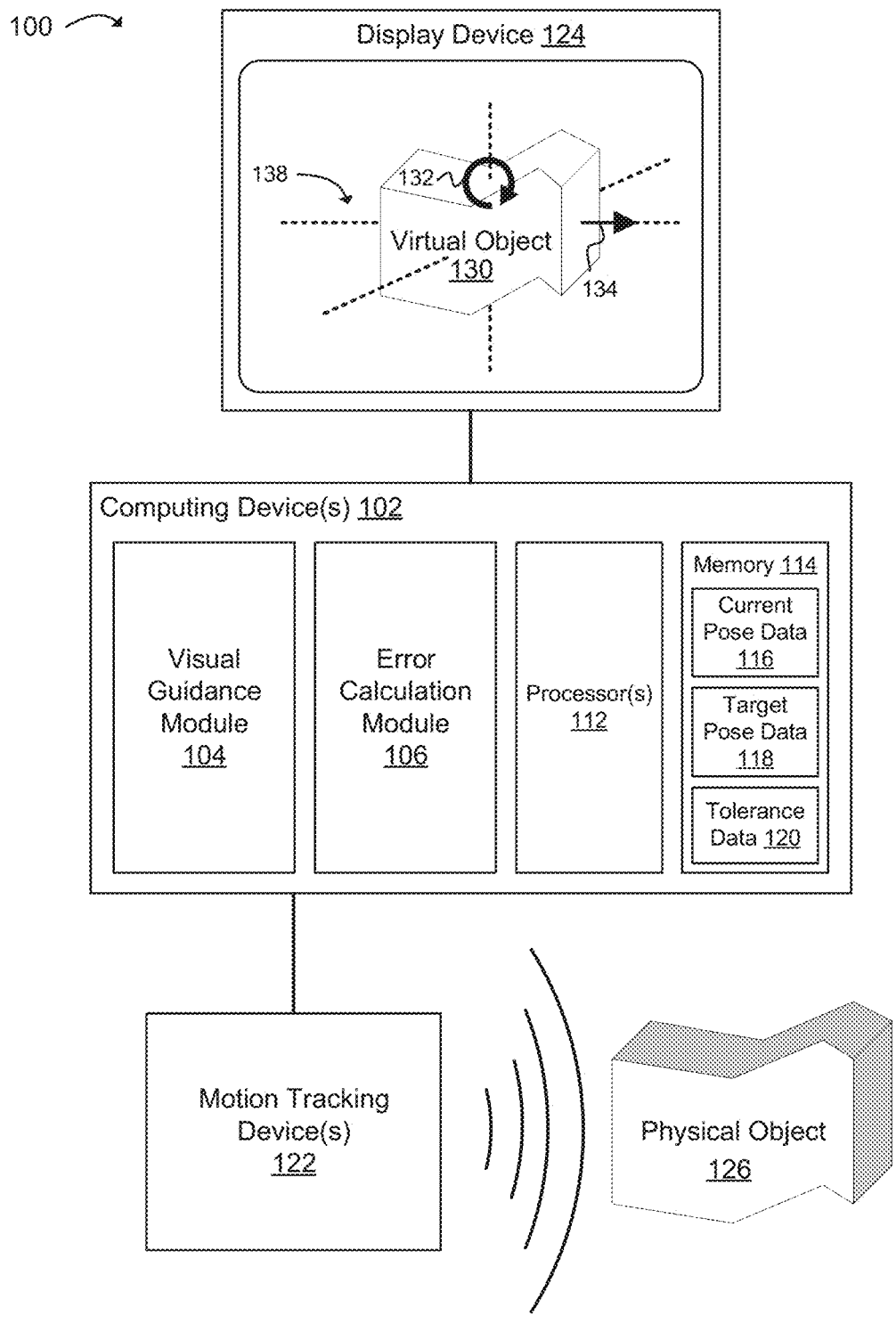
FIG. 1 is a block diagram illustrating an example of a visual guidance system for posing a physical object within three dimensional (3D) space.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a processor" includes reference to one or more of such devices and reference to "calculating" refers to one or more such steps.

As used herein, the term "about" is used to provide flexibility and imprecision associated with a given term, metric or value. The degree of flexibility for a particular variable can be readily determined by one skilled in the art. However, unless otherwise enunciated, the term "about" generally connotes flexibility of less than 1%, and most often less than 0.1%, and in some cases less than 0.01%.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "tolerance" refers to an allowable amount of variation in distance between a current translation and rotation distance and a target translation and rotation distance (e.g., 1 mm and 1 degree, respectively).

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of." For example, "at least one of A, B and C" explicitly includes only A, only B, only C, and combinations of each.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Examples of the Technology

The technology described herein relates to systems and methods for posing a physical object within three-dimensional (3D) space using translation and rotation cues that indicate a position and orientation to move the physical object to substantially align the physical object with a target pose. A method and system of visually communicating navigation instructions can use translational and rotational arrow cues (TRAC) defined in an object-centric frame while displaying a single principal view that approximates the human's egocentric view of the actual object. The target pose of the object is provided, but it is only used for the initial gross alignment. During the accurate-alignment stage, the user relies on the unambiguous arrow commands. In a series of human-subject studies, the TRAC method significantly outperforms the triplanar display in terms of time to complete 6-DoF navigation tasks, and that subjects can achieve submillimeter and subdegree accuracy using the TRAC method with a median completion time of less than 20 seconds.

As an example, a current position and orientation of a physical device can be obtained from a motion tracking system, and the current position and orientation can be used to calculate at least two of six degrees of freedom (6DoF) error based on a difference between the current position and orientation of the physical object and a target pose of the physical object. A virtual representation of the object and/or a coordinate frame representing the current position and orientation of the physical object can be output to a display to provide a visualization of a pose of the physical object in 3D space. Also, a translation cue and/or a rotation cue can be output to the display to indicate a direction to move the physical object to align the physical object with the target pose. The translation cue and the rotation cue can be provided as visual cues for posing the physical object to correspond to the target pose of the physical object. For example, the translation cue can indicate a translation direction to move the physical object along a translation axis of the physical object to align the position of the physical object with the target pose of the physical object. The rotation cue can indicate a rotation direction to move the physical object along a rotation axis of the physical object to align the orientation of the physical object with the target pose of the physical object. A user can follow the translation and rotation cues displayed on a display device and move the physical object into alignment with the target pose, whereupon an indication of success can be output, for example, to the display device and/or to an audio speaker.

To further describe the visual cue method, examples are now provided with reference to the figures. FIG. 1 is a block diagram illustrating an example of a visual guidance system 100 for posing a physical object 126 within 3D space. As illustrated, the system 100 can include a computing device 102 in communication with a motion tracking device(s) 122 and a display device 124. At a high level, the computing device 102 can be configured to receive current pose data 116 from the motion tracking device 122, and output to the display device 124, a virtual object 130 representing the physical object 126 and the current position and orientation of the physical object 126 as determined using the current pose data 116. The computing device 102 can calculate at least two of six degrees of freedom (6DoF) error based on a difference between the current position and orientation of the physical object 126 and a target pose of the physical object 126. The 6DoF error can be used to determine a translation direction and a rotation direction to move the physical object 126 to align a current pose of the physical object with the target pose of the physical object 126 within a tolerance. A tolerance (or acceptable error) can be an allowable amount of variation in distance between a current pose of a physical object 126 (e.g., a current translation and rotation distance) and a target pose of the physical object 126.

The computing device 102 can be configured to output a translation cue 134 and a rotation cue 132 to the display device 124. The translation cue 134 can indicate the translation direction to move the physical object 126 along a translation axis of the physical object 126 to align the position of the physical object 126 with the target pose of the physical object 126 within the tolerance. The rotation cue 132 can indicate the rotation direction to move the physical object 126 along a rotation axis of the physical object 126 to align an orientation of the physical object 126 with the target pose of the physical object 126 within the tolerance. A user can follow the directions provided by the translation cue 134 and the rotation cue 132 to manually move the physical object 126 in the translation direction and rotation direction indicated by the 6DoF error. The computing device 102 can be configured to analyze the current pose data 116 being received from the motion tracking device 122 to determine when a current pose of the physical object 126 aligns with the target pose of the physical object 126 within the tolerance, whereupon an indication of success can be provided to the user.

The computing device 102 can include modules that provide the functionality described above. The modules can include a visual guidance module 104, an error calculation module 106, and other modules. The visual guidance module 104 can be used to process pose data 116 received from the motion tracking device 122 and virtually replicate a current pose of a physical object 126 in 3D space using a virtual object 130, based on the current pose data 116 received from the motion tracking device 122. For example, the visual guidance module 104 may be used to analyze the current pose data 116 to determine a current position and orientation of the physical object 126, and the visual guidance module 104 can output the virtual object 130 to replicate the current position and orientation of the physical object 126. In another example, the visual guidance module 104 can output a coordinate frame 138 that is attached to the virtual object 130 to indicate a location of the virtual object 130 in 3D space. The coordinate frame 138 can include three linearly independent axes that are mutually orthogonal, such that the axes of the coordinate frame 138 can be aligned with visually perceptible axes of the virtual object 130, or displayed on the virtual object 130. In some examples, the coordinate frame 138 can include more than three axes, such that the axes span a three-dimensional vector space. In another example, the visual guidance module 104 can output the coordinate frame 138 without the virtual object 130, where the coordinate frame 138 can be used to represent the current pose of the physical object 126. As will be appreciated, any type of representation can be used to virtually represent the position and orientation of the physical object 126. Alternatively, an image of a physical object 126 can be captured using a camera device and the image can be output to the display device 124 along with visual cues 132/134 used to instruct a user to move the physical device 126 to a target pose.

In association with outputting a virtual representation of the physical object 126 to allow a user to visualize a current pose of the physical object 126, the visual guidance module 104 can be configured to output a translation cue 134 and/or a rotation cue 132 which can be used to visually provide instructions to a user for positioning and orienting the physical object 126 to substantially align with a target pose. In one example, a translation cue 134 can be provided as a graphical symbol that indicates a translation direction, such as a straight arrow. A rotation cue 132 can be provided as a graphical symbol that indicates a rotation direction, such as a round or circular arrow. FIG. 1 illustrates the translation cue 134 as being displayed as a straight arrow along a translation axis of the virtual object 130 and coordinate frame 138 to indicate a translation direction to move a physical object 126. The rotation cue 132 is illustrated as being displayed as a curved arrow along a rotation axis of the virtual object 130 and coordinate frame 138 to indicate a rotation direction to move the physical object 126. As will be appreciated, any type of graphical symbol can be used to represent a translation cue 134 and rotation cue 132. In some examples, highlighting, coloring, animation and the like can be used in relation to rotation and translation cues 132/134 to indicate a direction to move a physical object 126. Alternatively, a translation cue 134 and/or a rotation cue 132 can be provided as a message that instructs a user to move a physical object in a specified direction (e.g., "rotate clockwise" or "pull forward").

The visual guidance module 104 can output a translation cue 134 and/or a rotation cue 132 to the display device 124 based in part on a 6DoF error which can be calculated based on a difference between the current position and orientation of a physical object 126 and a target pose of the physical object 126. In one example, the visual guidance module 104 can obtain 6DoF error data from the error calculation module 106. The error calculation module 106 can be configured to calculate a 6DoF error using current pose data 116 received from the motion tracking device 122 and target pose data 118. Target pose data 118 can be used to define a target pose of a physical object 126. In one example, target pose data 118 can include position data and orientation data which define a position and orientation of a physical object 126. Illustratively, the position data and orientation data can be coordinates within a 3D space defining a target pose of a physical object 126. In one example, target pose data 118 can be updated before, during, or after substantial alignment of a physical object 126 with a target pose. For example, due to changing conditions, such as during a surgical procedure, a target pose of a physical object 126 may need to be changed. As such, target pose data 118 can be updated based on the changed conditions.

The error calculation module 106 can be used to calculate 6DoF error by determining a difference between a current position of a physical object 126 as indicated by current pose data 116 and a target pose of the physical object 126 as indicated by target pose data 118. The 6DoF error calculated by the error calculation module 106 can include a three degrees of freedom (3DoF) position error and a 3DoF orientation error for the axes of the physical object 126 which can be used by the visual guidance module 104 to determine a translation direction and/or a rotation direction to move the physical object 126 in order to align the pose of the physical object 126 with the target pose of the physical object 126.

After obtaining the 6DoF error data from the error calculation module 106, the visual guidance module 104 can evaluate the 6DoF error in relation to target pose data 118 and determine a translation direction and/or a rotation direction to move a physical object 126 in order to align a pose of the physical object 126 with the target pose of the physical object 126. For example, the visual guidance module 104 can evaluate a 3DoF position error and a 3DoF orientation error in relation to target pose data 118 to determine where in relation to a target pose a physical object 126 is located, and determine a translation direction and/or orientation direction to move the physical object 126 to align the physical object 126 with the target pose. The visual guidance module 104 can then output a translation cue 134 and/or a rotation cue 132 to the display device to visually indicate the translation direction and/or rotation direction to move the physical object 126. The visual guidance module 104 can continue to evaluate 6DoF error data obtained from the error calculation module 106 and output the translation cue 134 and/or the rotation cue 132 until the 6DoF error data indicates that a pose of the physical object 126 is aligned with a target pose of the physical object 126 within a tolerance.

In one example, output of a translation cue 134 and a rotation cue 132 to the display device can be provided based on a predetermined error correction scheme. Typically, one of a 3DoF position error and a 3DoF orientation error can be initially targeted and reduced until a desired tolerance is achieved. For example, the visual guidance module 104 can be configured to output a translation cue 134 or a rotation cue 132 to allow a user to align first aspect (position or orientation) of a physical object 126 with a target pose before aligning a second aspect (position or orientation) of the physical object 126 with the target pose. The visual guidance module 104 can determine which of a 3DoF position error (e.g. X, Y, or Z position) or which of a 3DoF orientation error is greater, and output a visual cue 132/134 associated with the greatest 3DoF position error (i.e., or 3DoF orientation error that has a largest error value as compared to one another). Illustratively, a difference between a 3DoF position errors can be determined by calculating a distance from the target position and choosing the largest distance. Based on updated current pose data 116, each of the unrestrained 3DoF position errors can be iteratively recalculated and compared to the target pose data 118 until a desired position tolerance is achieved for each of the 3DoF position errors (or fewer in the case of 1 or 2DoF position corrections). The process can then be repeated for orientation errors. Typically, orientation corrections can precede position corrections, although the reverse can be performed in some cases. Acceptable tolerance can depend largely on the specific application. However, in some examples, position tolerance can be less than about 10 mm, and in some cases less than 1 mm. Similarly, common orientation or rotation tolerance can be less than about 5°, and in some cases less than about 1°.

In one example, the visual guidance module 104 can output a visual cue 134 associated with the greatest 3DoF position error until each of the 3DoF position errors is within a target position tolerance, whereupon the visual guidance module 104 can switch to the next visual cue 132 associated with the greatest 3DoF orientation error. As an illustration, the visual guidance module 104 may determine that an x coordinate 3DoF position error is greater than y and z coordinate 3DoF position errors. In response, the visual guidance module 104 may output a translation cue 132 to the display device 124 to instruct a user to move a physical object 126 in an x direction indicated by the translation cue 134. Updated current pose data 116 can then be compared with target pose data 118 to determine which, if any, of the 3DoF position errors is within a desired position tolerance. After determining that each of the 3DoF position errors is within the desired tolerance, the visual guidance module 104 may stop outputting the translation cue 1342 and output an orientation cue 132 to the display device 124 to instruct the user to move the physical object 126 in an orientation indicated by the orientation cue 132 until each of the 3DoF orientation errors is within the target rotation tolerance. At this point, if each of the degrees of freedom for both the position and orientation of the physical object 126 are within the tolerance, the visual guidance module 104 may stop outputting the orientation cue 132 and output an indication that the physical object 126 aligns with the target pose. However, in the event that either of the position and orientation of the physical object 126 falls out of the tolerance of the target pose, the visual guidance module 104 can again output a visual cue 132/134 associated with the position or orientation of the physical object 126 that is outside of the tolerance of the target pose.

Thus, the visual guidance module 104 can output the visual cue 132/134 associated with the greatest 3DoF error until the 3DoF error is less than another 3DoF error, and then switch output to another visual cue 132/134 associated the greatest 3DoF error. As one example, the visual guidance module 104 can be configured to identify a 3DoF position error associated with a 3DoF position axis that is greater than other 3DoF position errors associated with other 3DoF position axes and output a translation cue linked to the greatest 3DoF position error to the display device 124. Output of translation cues 134 for 3DoF position axes can be alternated such that one translation cue 134 associated with the greatest 3DoF position error can be displayed on the display device 124 at a time. In yet another example, the visual guidance module 104 can output both a rotation cue 132 and a translation cue 134.

Figure 2:
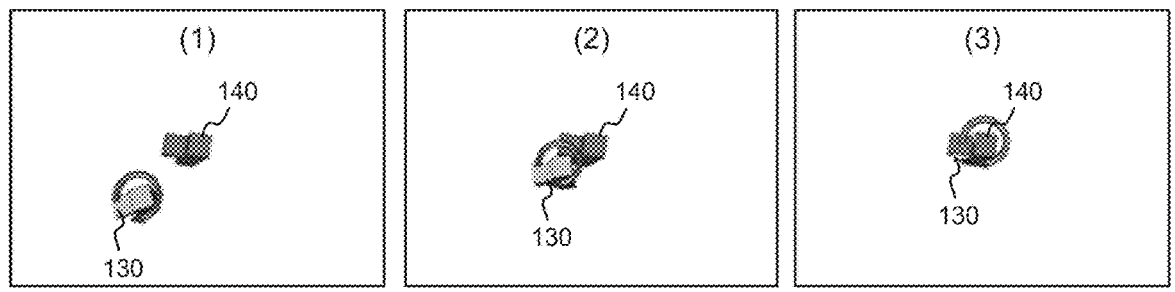
FIG. 2 is a series of diagrams that illustrate aligning a first virtual object that represents a current pose of a physical object with a second virtual object that represents a target pose of the physical object.

In some examples the visual guidance module 104 can be configured to output a virtual representation of a physical object 126 in a target pose. For example, as illustrated in FIG. 2, a virtual object 130 representing a current pose of a physical object 126 can be output along with a virtual target object 140 to the display device 124. A user can use the virtual target object 140 as a reference and move the physical object 126 to match the pose of the virtual target object 140. As illustrated in FIG. 2, the virtual pose of the virtual object 130 can be updated and output to the display device 124 to reflect the current pose of the physical object 126 as indicated by current pose data 116 received from the motion tracking device 122. Also, a visual cue 132/134 can be output with the virtual object 130 to indicate a direction (translation and/or rotation direction) to move the physical device 126.

Figure 3A:
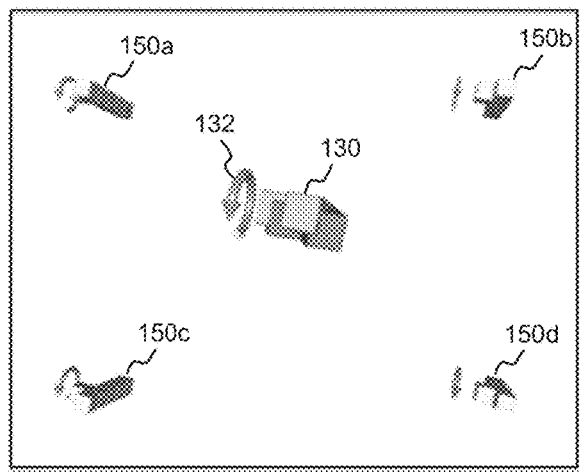
FIGS. 3a and 3b are diagrams that illustrate alternative perspectives of a virtual object which can be output to a display along with the virtual object.
Figure 3B:
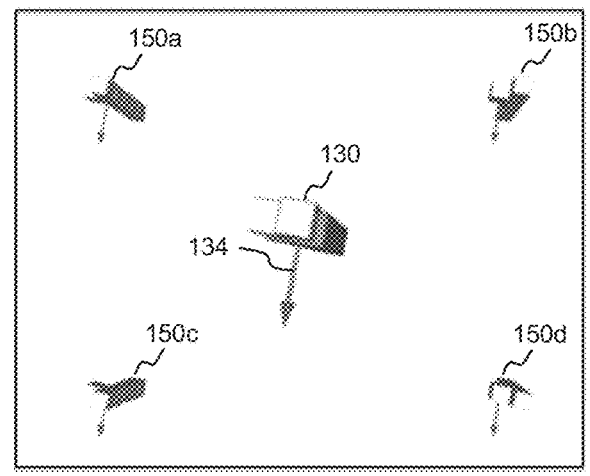

Returning to FIG. 1, in some examples the visual guidance module 104 can be configured to output alternative perspectives of the virtual object 130 with visual cues 132/134 to the display device 124 to provide additional views of the virtual object 130 and visual cues 132/134. For example, as illustrated in FIGS. 3A and 3B, a virtual object and visual cue 132/134 can be output to the display device 124 along with alternative perspectives 150*a-b* of the virtual object 130 in order to mitigate a risk of obscuring a virtual cue 132/134 with the virtual object 130 in certain virtual poses of the virtual object 130.

Returning again to FIG. 1, the visual guidance module 104 can be configured detect when a physical object 126 is substantially aligned with a target pose of the physical object 126. For example, as mentioned above, the visual guidance module 104 can detect when a 6DoF error is within a tolerance. In some examples, detecting that at least two of the 6DoF errors are within a tolerance of a target pose may be an indication that a physical object 126 is substantially aligned with the target pose. For example, a number of degrees of freedom used to define a target pose may be based in part on a procedure and/or an instrument used to perform the procedure. As an example, in image-guided surgery where one or more degrees of freedom may be fixed (e.g., as in laparoscopic surgery where a surgical instrument may be limited to fewer than six degrees of freedom), detecting that non-fixed degrees of freedom are within a tolerance can indicate alignment of a current pose with a target pose. In such cases where one or more of the 6DoF are restrained, the above described iterative comparison process can be truncated to include only those unrestrained degrees of freedom.

As described earlier, a tolerance may be an allowable amount of variation in distance between a current pose of a physical object 126 and a target pose of the physical object 126. For example, tolerance data 120 can define a sufficiently accurate alignment between a physical object 126 and a target pose defined by target pose data 118. A tolerance may be based in part on a size, weight, or type of physical object 126, or a procedure being performed in association with a physical object 126. In one example, the computing device 102 can be preprogrammed with a tolerance (i.e., tolerance data 120) stored in memory 114 for use by the visual guidance module 104. In another example, a user can provide a tolerance for use by the visual guidance module 104. In yet another example, a user may provide a tolerance value that can be used in place of preprogrammed tolerance data 120. As will be appreciated, a number of tolerances can be defined, including a position tolerance and a rotation tolerance. After detecting that a physical object 126 is substantially aligned with a target pose of the physical object 126, the visual guidance module 104 can output an indication of success, including: a message indicating successful alignment, a visual indication of successful alignment (e.g., changing a color of a virtual object 130 from red to green, flashing animation of the virtual object, stop output of visual cues 132/134, etc.), an audio signal (e.g., a tone, beep, chime, etc.), haptic feedback, as well as other indications of success.

A physical object 126 can include, but is not limited to, a surgical instrument, a medical device being positioned with respect to a patient undergoing a medical procedure, such that the medical device may be rigidly fixed with respect to the patient after alignment of the medical device, an ultrasound probe, a sensor, a body part, such as a limb segment, a finger segment, or a head, a haptic interface, a device used to direct a cinematic filming device or prop, a component of a musical instrument, a piece of athletic equipment (e.g., a racquet, club, ball, ski, board, bicycle, etc.), a segment of a kinematic linkage or robot, as well as other physical objects. As a result, from one to four of the 6DoF can be fixed. In such cases, only a limited subset of 6DoF errors need to be calculated (e.g. two, three, four or five).

A computing device 102 may comprise a processor-based system having at least one processor 112 and computer memory 114. A computing device 102 may be a device such as, but not limited to, a desktop computer, laptop or notebook computer, tablet computer, mainframe computer system, workstation, network computer, server, virtual machine, or other devices with like capability. A display device 124 can include any device capable of receiving output from the computing device 102 and displaying the output to a display. A display device 124 can include, but is not limited to, a two-dimensional (2-D) display, such as a computer monitor, a 3D display, such as virtual reality goggles, a computer monitor with shutter glasses, or other forms of virtual or augmented reality displays. A display device 124 can be connected to the computing device 102 via a wired connection or a wireless connection using an appropriate communication interface, or connected via a network, such as a local area network (LAN), wide area network (WAN) 312, the Internet, or other computing network.

A motion tracking device 122 can include, but is not limited to, an optical motion tracker, an electromagnetic motion tracker, a kinematic linkage comprising joint sensors, such as potentiometers or optical encoders, or a sensor mounted on a physical object 126, such as an inertial measurement unit, a rate gyroscope, or a magnetic compass. As will be appreciated, a number of motion tracking devices 122 can be used to track a position and orientation of a physical object 126, where the motion tracking devices 122 may form a motion tracking system. The motion tracking device 122 can be connected to the computing device 102 via a wired connection or a wireless connection using an appropriate communication interface. In some examples, the motion tracking device 122 can be in network communication with the computing device 102 via a local area network (LAN), wide area network (WAN) 312, the Internet, or other computing network. In one example, the motion tracking device 122 may send the current pose data 116 in a data stream, and the visual guidance module 104 can use the current pose data 116 received in the data stream to continuously update a virtual pose of the virtual object 130 and/or the coordinate frame 138 to correspond to a current pose of the physical object 126. As such, changes made to the pose of the physical object 126 detected by the motion tracking device 122 can be made to the virtual pose of the virtual object 130 and/or the coordinate frame 138, allowing a user to visualize changes to the pose of the physical object 126.

FIG. 1 illustrates that certain processing modules may be discussed in connection with this technology and these processing modules may be implemented as computing services. In one example configuration, a module may be considered a service with one or more processes executing on a server or other computer hardware. Such services may be centrally hosted functionality or a service application that may receive requests and provide output to other services or consumer devices. For example, modules providing services may be considered on-demand computing that are hosted in a server, virtualized service environment, grid or cluster computing system. An API may be provided for each module to enable a second module to send requests to and receive output from the first module. While FIG. 1 illustrates an example of a system environment that may implement the techniques above, many other similar or different environments are possible. The example environment discussed and illustrated above is merely representative and not limiting.

Figure 4:
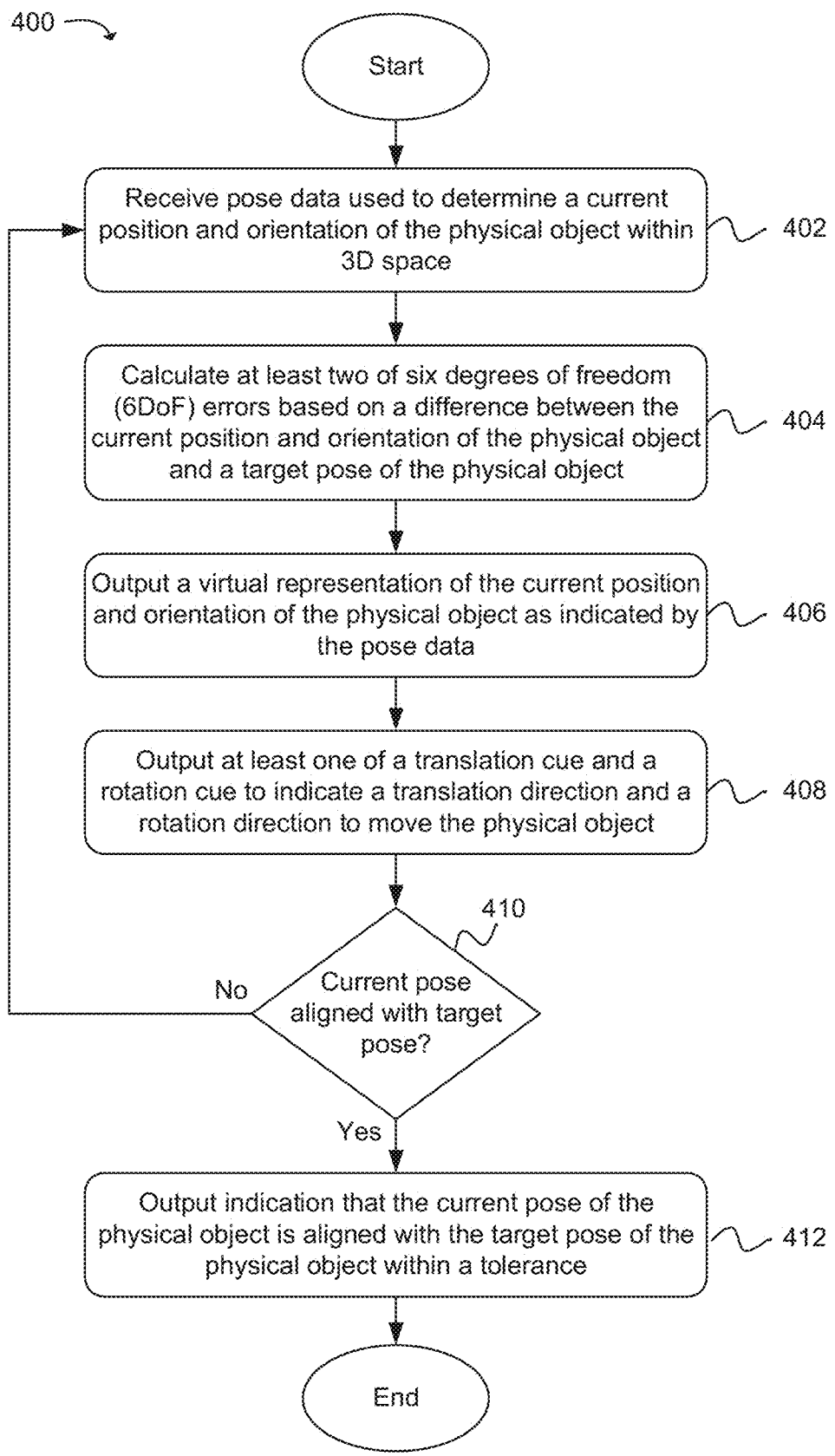
FIG. 4 is a flow diagram illustrating an example method for posing a physical object in 3D space.

FIG. 4 is a flow diagram that illustrates an example method 400 for posing a physical object in 3D space. As in block 402, pose data can be received, for example, from a motion tracking system, and the pose data can be used to determine a current position and orientation of a physical object within 3D space. Illustratively, a motion tracking system can include at least one of an optical motion tracker, an electromagnetic motion tracker, a kinematic linkage comprising joint sensors, and/or a sensor mounted on the physical object. The motion tracking system can provide a data stream used to continuously update a virtual pose represented by a virtual representation, such as a virtual object or a coordinate frame. The pose data can include position data and orientation data, such as coordinate data, that indicates a substantially current position and orientation of the physical object. The pose data can provide a view of the physical object used to generate a virtual view of the physical object. In one example, a virtual view of the physical object can substantially correspond to a user view or user perspective of the physical object. In another example, various virtual views of the physical object can be generated, such that a user can select from the various virtual views.

As in block 404, at least two of six degrees of freedom (6DoF) errors can be calculated based on a difference between a current position and orientation of the physical object and a target pose of the physical object. The two or more 6DoF errors can be used to determine a translation direction and a rotation direction to move the physical object to align a current pose of the physical object with the target pose of the physical object within a tolerance. For example, the DoF errors can include a three degrees of freedom (3DoF) position error and a 3DoF orientation error which can be used to determine a translation direction and a rotation direction to move the physical object, as described earlier.

As in block 406, a virtual representation of the current position and orientation of the physical object can be output to a display as a virtual pose indicated by the pose data. The virtual representation can include: a virtual object that represents the physical object and the current position and orientation of the physical object, a coordinate frame that represents the current position and orientation of the physical object, or the coordinate frame attached to the virtual object, such that the virtual object can be output to overlay the coordinate frame. The display can include any display device capable of showing visual output, including 2-D displays and 3-D displays. In one example, multiple virtual objects comprising multiple views of the physical object can be output to the display. The multiple virtual objects can provide a user with alternative perspectives of the virtual object in order to mitigate a risk of obscuring a translation cue or rotation cue with the virtual object in certain virtual poses of the virtual object.

As in block 408, at least one of a translation cue and a rotation cue that indicate a translation direction and a rotation direction to move the physical object can be output to the display. The translation cue can be used to indicate the translation direction to move the physical object along a translation axis of the physical object to align a position of the physical object with the target pose of the physical object within the tolerance. The rotation cue can be used to indicate the rotation direction to move the physical object along a rotation axis of the physical object to align an orientation of the physical object with the target pose of the physical object within the tolerance. The translation cue and the rotation cue can be visual cues for posing the physical object to correspond to the target pose of the physical object within the tolerance.

In one example, a visual cue output to the display can be selected based on a 3DoF error (i.e. either position or orientation) linked to the visual cue that is greater than other 3DoF errors linked to other visual cues. As one example, the method 400 can determine which one of a 3DoF position error (or a 3DoF orientation error) is greater and output the translation cue to the display for the particular position direction that is greatest, or output the rotation cue to the display for the greatest orientation error. In one example, a difference between each of the unrestrained 3DoF position errors can be determined by calculating a difference between a current 3DoF position and a target position to produce a position error (e.g. X, Y and Z position errors), and comparing the magnitudes to identify which of the 3DoF position errors is greatest. As previously described, a similar comparison can be made for orientation errors either before, after, or contemporaneously with position errors. A visual cue (translation cue or rotational cue) associated with the greatest 3DoF errors can then be output to the display.

As another example, the method 400 can identify a greatest 3DoF position error for a translation axis that is greater than other 3DoF position errors for other translation axes and output the translation cue linked to the greatest 3DoF position error to the display. The method 400 can alternate output between the translation cues based on the greatest 3DoF position error. As an illustration, as part of a determination that a 3DoF position error for the X-axis (Surge) is greater than 3DoF position errors for the Y-axis (Sway) and Z-axis (Heave), an X-axis translation cue can be output to the display to instruct a user to move the physical object in a translation direction indicated by the X-axis translation cue. After moving the physical object as indicated by the X-axis translation cue, output of the X-axis translation cue can stopped, and the current greatest 3DoF position error can be identified (e.g., the 3DoF position error for the Y-axis) and the translation cue (e.g., Y-axis translation cue) linked to the greatest 3DoF position error can be output to the display. Accordingly, output of the translation cues (e.g., X, Y, and Z axes translation cues) can be alternated until each 3DoF position error is aligned with the target pose within the target position tolerance. Thereafter, if any of the 3DoF orientation errors is not within the orientation tolerance of the target pose, a corresponding rotation cue can be displayed.

Also, the method 400 can identify a greatest 3DoF orientation error for a rotation axis that is greater than other 3DoF orientation errors for other rotation axes and output the rotation cue linked to the greatest 3DoF orientation error to the display. The method 400 can alternate output between the rotation cues based on the greatest 3DoF orientation error. As an illustration, as part of a determination that a 3DoF orientation error for the Z-axis (Yaw) is greater than 3DoF orientation errors for the X-axis (Roll) and Y-axis (Pitch), a Z-axis rotation cue can be output to the display to instruct a user to move the physical object in a rotation direction indicated by the Z-axis rotation cue. After moving the physical object as indicated by the Z-axis rotation cue, output of the Z-axis rotation cue can stopped, and the current greatest 3DoF orientation error can be identified (e.g., the 3DoF orientation error for the Y-axis) and the rotation cue (e.g., Y-axis translation cue) linked to the greatest 3DoF orientation error can be output to the display. Accordingly, output of the rotation cues (e.g., X, Y, and Z axes rotation cues) can be alternated until each 3DoF orientation error is aligned with the target pose within the tolerance. Thereafter, if any of the 3DoF translation errors is not within the tolerance of the target pose, a translation cue can be displayed.

In one example, the translation cue can be displayed as a straight arrow along a translation axis of a coordinate frame to indicate the translation direction to move the physical object, and the rotation cue can be displayed as a curved arrow along the rotation axis of the coordinate frame to indicate the rotation direction to move the physical object. As will be appreciated, any symbol that indicates a direction can be used to as a translation cue or a rotation cue. In some examples, the translation cue and the rotation cue can be animated to indicate a direction to move the physical object.

In some examples, a virtual representation of the target pose can be output to the display to provide a user with a visual representation of the target pose. The virtual representation of the target pose can comprise a virtual object in the target pose of the physical object, which can be output to a display to assist a user in performing an initial gross alignment of the physical object. For example, a first virtual object can be output to a display to represent a target pose of a physical object, and a second virtual object can be output to the display to represent a current pose of the physical object. A user can reference the first virtual object to perform a gross alignment of the physical object with the target pose, while referencing the second virtual object to monitor the current position of the physical object as the gross alignment is performed. After performing the initial gross alignment of the physical object, the user can follow the instructions provided by the translation and rotation cues to align the position and orientation of the physical object within a tolerance of the target pose. A tolerance or acceptable error can be an allowable amount of variation in distance between the current pose of the physical object and the target pose of the physical object.

The method 400 can monitor a current pose of the physical object via pose data received from the motion tracking system to determine whether the current pose of the physical object corresponds to the target pose of the physical object within the tolerance. A number of degrees of freedom used to define a target pose may be based in part on a procedure and/or an instrument used to perform the procedure. For example, a procedure where one or more degrees of freedom may be fixed, non-fixed degrees of freedom may be used to define a target pose. Thus, the method 400 can monitor the pose data to determine whether a number of 6DoF errors (e.g., two, three, four, five, or six) defined by the target pose are within a tolerance of the target pose.

As in block 410, in the case that the current pose of the physical object corresponds to the target pose of the physical object within the tolerance, then as in block 412, an indication of success that the current pose of the physical object corresponds to the target pose of the physical object can be provided to the user. Non-limiting examples of indication of success can include: outputting a message to a display indicating successful alignment of a physical object with a target pose, outputting a visual indication (e.g., changing a color of a virtual object from red to green, flashing an animation of the virtual object, discontinue output of translation and rotation cues, etc.) to a display, outputting an audio signal (e.g., a tone, beep, chime, etc.) to an audio speaker, outputting haptic feedback to a control device (e.g., a console of a surgical robot), as well as other types of output which indicate successful alignment of a physical object with a target pose. Referring again to block 410, in the case that the current pose is not aligned with the target pose, the method 400 can continue to monitor pose data received from the motion tracking system to determine whether a current pose aligns with the target pose.

Figure 5:
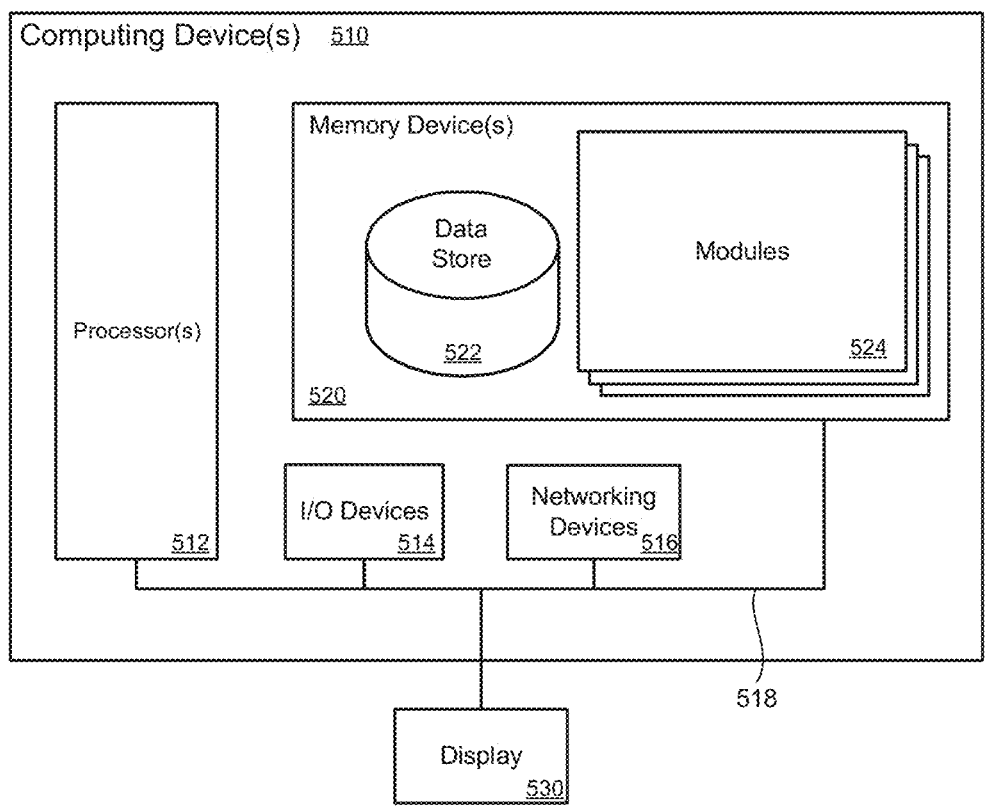
FIG. 5 is block diagram illustrating an example of a computing device that may be used to execute a method for posing a physical object in 3D space.

FIG. 5 illustrates a computing device 510 on which modules of this technology can execute. A computing device 510 is illustrated on which a high level example of the technology can be executed. The computing device 510 can include one or more processors 512 that are in communication with memory devices 520. The computing device 510 can include a local communication interface 518 for the components in the computing device. For example, the local communication interface 518 can be a local data bus and/or any related address or control busses as may be desired.

The memory device 520 can contain modules 524 that are executable by the processor(s) 512 and data for the modules 524. In one example, the memory device 520 can include a visual guidance module, an error calculation module, and other modules. The modules 524 may execute the functions described earlier. A data store 522 can also be located in the memory device 520 for storing data related to the modules 524 and other applications along with an operating system that is executable by the processor(s) 512.

Other applications can also be stored in the memory device 520 and may be executable by the processor(s) 512. Components or modules discussed in this description that can be implemented in the form of software using high-level programming languages that are compiled, interpreted or executed using a hybrid of the methods.

The computing device 510 can also have access to I/O (input/output) devices 514 that are usable by the computing device 510. Output generated by the computing device 510 can be provided to a display 530 and other output devices. Networking devices 516 and similar communication devices may be included in the computing device 510. The networking devices 516 can be wired or wireless networking devices that connect to the internet, a LAN, WAN, or other computing network.

The components or modules that are shown as being stored in the memory device 520 can be executed by the processor(s) 512. The term "executable" may mean a program file that is in a form that may be executed by a processor 512. For example, a program in a higher level language may be compiled into machine code in a format that may be loaded into a random access portion of the memory device 520 and executed by the processor 512, or source code can be loaded by another executable program and interpreted to generate instructions in a random access portion of the memory to be executed by a processor. The executable program can be stored in any portion or component of the memory device 520. For example, the memory device 520 may be random access memory (RAM), read only memory (ROM), flash memory, a solid state drive, memory card, a hard drive, optical disk, floppy disk, magnetic tape, or any other memory components.

The processor 512 may represent multiple processors and the memory device 520 may represent multiple memory units that operate in parallel to the processing circuits. This can provide parallel processing channels for the processes and data in the system. The local communication interface 518 can be used as a network to facilitate communication between any of the multiple processors and multiple memories. The local communication interface 518 can use additional systems designed for coordinating communication such as load balancing, bulk data transfer and similar systems.

While the flowcharts presented for this technology may imply a specific order of execution, the order of execution may differ from what is illustrated. For example, the order of two more blocks may be rearranged relative to the order shown. Further, two or more blocks shown in succession may be executed in parallel or with partial parallelization. In some configurations, one or more blocks shown in the flow chart may be omitted or skipped. Any number of counters, state variables, warning semaphores, or messages might be added to the logical flow for purposes of enhanced utility, accounting, performance, measurement, troubleshooting or for similar reasons.

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules can also be implemented in software for execution by various types of processors. An identified module of executable code may, for instance, comprise one or more blocks of computer instructions, which may be organized as an object, procedure, or function. Nevertheless, the executables of an identified module need not be physically located together, but may comprise disparate instructions stored in different locations which comprise the module and achieve the stated purpose for the module when joined logically together.

Indeed, a module of executable code can be a single instruction, or many instructions and can even be distributed over several different code segments, among different programs and across several memory devices. Similarly, operational data can be identified and illustrated herein within modules and may be embodied in any suitable form and organized within any suitable type of data structure. The operational data may be collected as a single data set, or may be distributed over different locations including over different storage devices. The modules may be passive or active, including agents operable to perform desired functions.

The technology described here can also be stored on a computer readable storage medium that includes volatile and non-volatile, removable and non-removable media implemented with any technology for the storage of information such as computer readable instructions, data structures, program modules, or other data. Computer readable storage media include, but is not limited to, a non-transitory machine readable storage medium, such as RAM, ROM, EEPROM, flash memory or other memory technology, CD-ROM, digital versatile disks (DVD) or other optical storage, magnetic cassettes, magnetic tapes, magnetic disk storage or other magnetic storage devices, or any other computer storage medium which may be used to store the desired information and described technology.

The devices described herein can also contain communication connections or networking apparatus and networking connections that allow the devices to communicate with other devices. Communication connections are an example of communication media. Communication media typically embodies computer readable instructions, data structures, program modules and other data in a modulated data signal such as a carrier wave or other transport mechanism and includes any information delivery media. A "modulated data signal" means a signal that has one or more of its characteristics set or changed in such a manner as to encode information in the signal. By way of example and not limitation, communication media includes wired media such as a wired network or direct-wired connection and wireless media such as acoustic, radio frequency, infrared and other wireless media. The term computer readable media as used herein includes communication media.

Reference was made to the examples illustrated in the drawings and specific language was used herein to describe the same. It will nevertheless be understood that no limitation of the scope of the technology is thereby intended. Alterations and further modifications of the features illustrated herein and additional applications of the examples as illustrated herein are to be considered within the scope of the description.

Furthermore, the described features, structures, or characteristics may be combined in any suitable manner in one or more examples. In the preceding description, numerous specific details were provided, such as examples of various configurations to provide a thorough understanding of examples of the described technology. It will be recognized, however, that the technology may be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements may be devised without departing from the spirit and scope of the described technology.

Example Experiments Using the Present Technology

A study was conducted which included three human-subject experiments to evaluate the performance of the present technology, which is referred to below as the "visual cue method". In general, users quickly perform a gross alignment of a physical object with a target pose without using the visual cues. As a result, these experiments were conducted with a primary interest in the second, accurate-alignment stage. Throughout, performance was quantified using the completion time to perform a 6-DoF alignment task to within some specified tolerance.

In the first experiment, two different methods of presenting the arrow cues to the user are presented, considering 3-DoF position alignment and 3-DoF orientation alignment separately. In both cases, arrow cues were shown in object-centric axes. However, in one case all three arrows were shown simultaneously, and in one case only the arrow corresponding to the largest error was shown (and kept showing the arrow until that DoF was within the specified tolerance). Showing a single arrow at a time resulted in faster alignment times as opposed to showing all three arrows at a time, for both position and orientation. It should also be noted that, a third option in which only the arrow corresponding to the largest error at any given instant in time is shown can be used, although the resulting rapid switching between arrow cues can be confusing for some users.

In the second experiment, the visual cue method was compared with a triplanar display for 6-DoF navigation tasks. The visual cue method resulted in faster alignment times than the triplanar display. In addition, the worst-case outliers seen when using the triplanar display were substantially slower than the worst-case outliers seen when using the visual cue method. The experiment utilized subjects without any prior training with either method, indicating that the visual cue method appears inherently more intuitive than the triplanar display.

In the final experiment, the time-accuracy trade-off is characterized when using the visual cue method. Subjects were able to achieve submillimeter and sub-degree accuracy with a median completion time of less than 20 sec. Additionally, subjects showed a significant improvement in the second half of the experiment compared to the first half, which were separated by two days, indicating that training with the visual cue method results in significant improvement over the technology's already intuitive first use.

Figure 6:
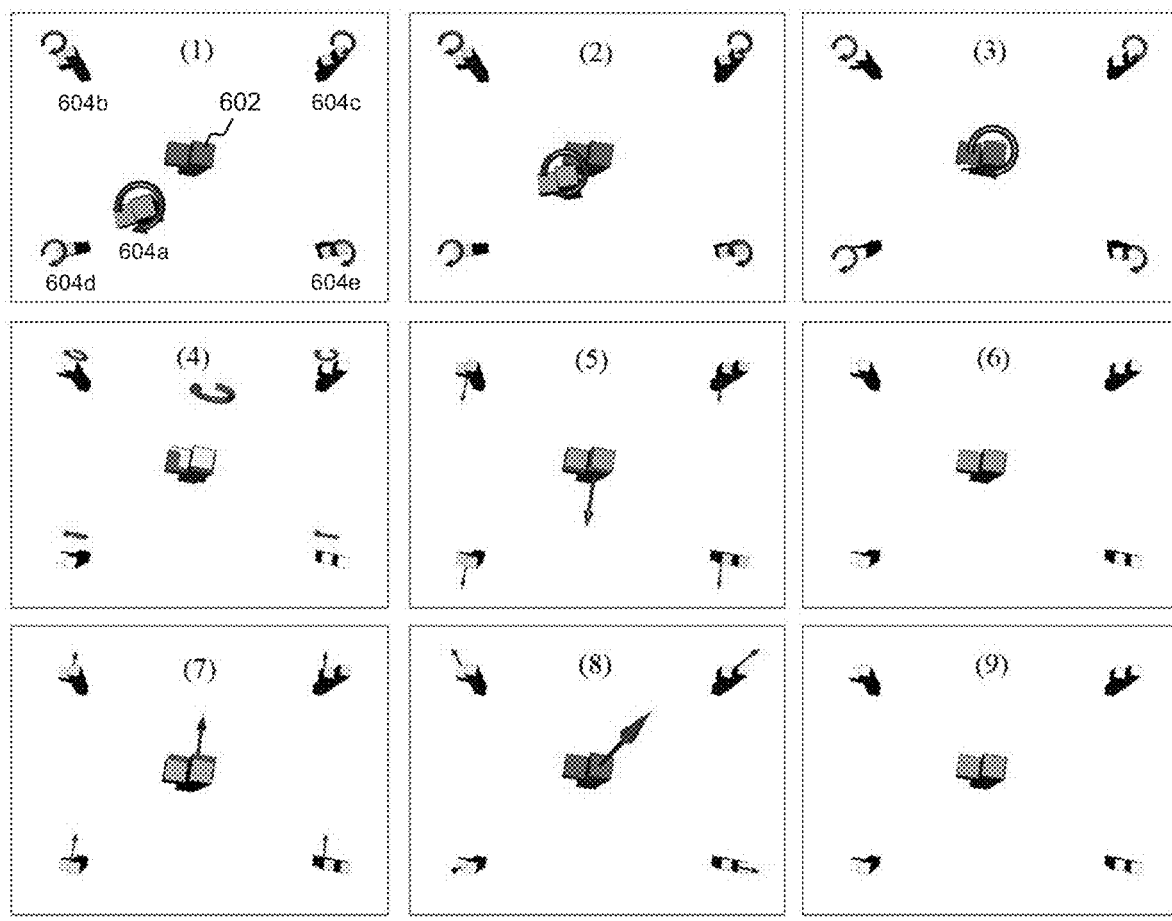
FIG. 6 is a schematic representation of a typical navigation task using a visual cue method.

FIG. 6 is a schematic representation of a typical navigation task using the visual cue method. A target object 602 is the target pose. Virtual objects 604a-e move with a hand-held object, where a main object 604a in the center of frames (1) to (3) both translates and rotates, but the four alternate views of the main object (604b-e) in the corners of frames (1) to (9) rotate with fixed positions. In the example illustrated in FIG. 6, a user performs a gross alignment from frames (1) to (3) without using arrow cues. Thereafter, using a single arrow cue at a time, the user converges on the target pose by frame (6), which can be indicated by changing the color of the main object 604a, but does not maintain a 6-DoF pose within a specified tolerance, so the arrow cues continue until the user converges on the target pose again in frame (9).

Experiment 1

A human-subject study was conducted using four adult males and four adult females. The subjects had normal (corrected) vision and normal motor functions by self-report. The experiment was divided into two sessions. Session A was designed to evaluate pure rotational guidance, and translation was ignored. A Polaris Spectra (Northern Digital Inc.) optical tracker was used to detect position and orientation of an unconstrained object. The object was chosen because it has three clearly discernible orthogonal axes. Retroreflective spheres were attached to one end of the object for 6-DoF pose tracking by the optical tracker.

Session B was designed to evaluate pure translational guidance, and rotation was constrained. An Entact W6D 6-DoF haptic device was used. An object of identical shape and size to the object in Session A was used, but the object was directly attached to the haptic device, such that forces and torques could be applied to it by the haptic device.

For both sessions, a 483 mm (19 in) desktop monitor was positioned 3.83 m (6 ft) in front of a subject sitting at a table. The Polaris system was placed above the monitor, for tracking in Session A. For Session B, the Entact haptic device was positioned on the table. The haptic device was programmed to restrict object rotation using a stiff 3-DoF rotational spring. This enabled performance of pure-translation experiments without the confounding factor of rotation, which was not possible with the unconstrained device. The height of the chair and the placement of the haptic device were adjusted for each subject so that they could comfortably rest their elbows on the table or the armrests of the chair.

Figure 7:
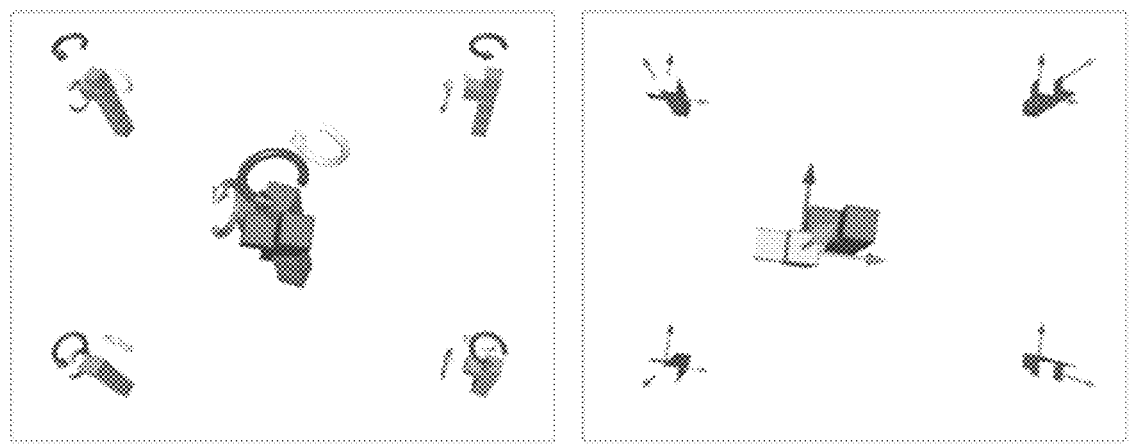
FIG. 7 is a schematic representation of Experiment 1 involving a typical navigation task using the visual cue method.
Figure 7:
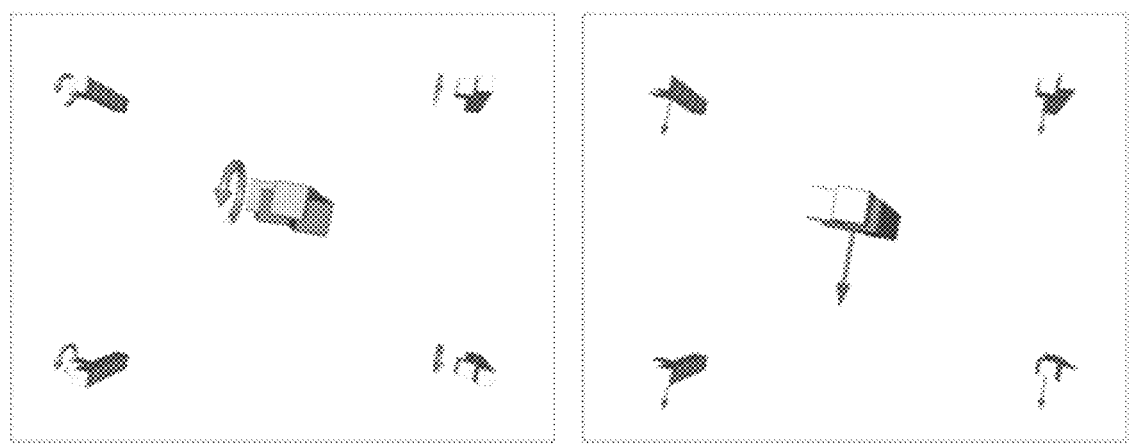

The experiment used a counterbalanced approach in a repeated-measures design, examining completion time to match a virtual object, whose movement was controlled by the physical object, to a static virtual target pose using virtual arrow cues. There are many possible variations of presenting intuitive arrow cues as guidance. Two methods that were found to be intuitive were tested. Both involved displaying arrows along object-centric axes of the manipulated object, with Session A displaying rotational (circular) arrows and Session B displaying translational (straight) arrows. The first method presents all (up to three) arrows simultaneously and individual arrows disappear when they fall within the given convergence bounds, as shown in FIG. 7(a). The second method presents a single arrow at a time to direct user movement, as shown in FIG. 7(b). The arrow corresponding to the single DoF with the largest error until convergence in that DoF, at which point a switch to the new arrow corresponding to the largest error was made, iterating until all three DoF had converged. These methods are referred to as the all-arrows (AA) method and single-arrow (SA) method, respectively.

Sessions were counterbalanced equally between male and female subjects: two male and two female subjects began with Session A and the remaining four subjects began with Session B. Session A measured completion time T, displaying only rotational arrows; the position of the virtual object was locked in the center of the monitor, and translations of the physical object had no effect on the virtual object. Session B measured T, displaying only translational arrows, using the Entact haptic device to restrict rotation using a stiff rotational virtual spring, implemented as a proportional-derivative (PD) controller. Sessions were separated by two days to mitigate effects of learning and fatigue. Each session lasted 29-57 minutes.

A set of 30 target poses were randomly generated for use in both sessions. For each pose, translational offsets were assigned along each of the three principal axes drawn from uniform distributions in the range 40 mm from the home position, and a rotational offset of 15 was assigned (using the angle-axis formulation) about an axis drawn from a uniform distribution on the sphere. The rotational and translational offsets were chosen to test the accurate-alignment stage rather than the gross-alignment stage. The same 30 target poses were used in both sessions and for all subjects, and were each used once for each of the SA and AA methods. This amounted to a total of 60 target poses per session. The order of the 60 target poses was randomized for each session and subject, in order to mitigate the effects of learning or fatigue.

A generalized linear regression analysis was used to determine statistical significance of treatment factor arrow method (treated as a fixed-effect variable) on the response completion time T, using blocking factors subject (treated as random-effect variable) and session order (treated as fixed-effect variable). The conventional significance for the entire analysis was determined at=0:05.

In each session, two virtual objects similar to the object held by the subject appeared on a monitor. One acted as a stationary target pose to be matched. The second moved as directed by the physical object guided by the subject. Subjects were instructed to move the object to the target pose (orientation or position, respectively) as quickly as possible. Subjects were instructed to perform gross alignment first, and then use the given arrow cues to perform the final alignment. Additional instructions related to avoiding camera workspace boundaries were given. Each session was preceded by a short training stage in which the subject became familiar with the method before data collection began. Each session was separated into four sub sessions, and subjects were instructed to take a break after each sub session for at least 30 seconds (but longer if desired) to avoid effects of fatigue. At the start of each sub session, the subject completed two trials that were not recorded and did not count toward the 15 poses of that sub session.

At the start of each trial, the subject homed the object to a specified homing position, and then moved the object to match the target pose as quickly as possible. Homing was performed before every pose to ensure that the object would not go out of range of the tracking system due to rotational or translational drift. To ease the burden of homing on the subject in Session A, the required pose matching thresholds during homing were relaxed so that homing could be accomplished quickly; this should have negligible effect on the results, due to the initial gross-alignment stage. In Session B, the haptic device automatically homed the device for each trial and then automatically configured itself to its desired orientation.

During each trial, when the object was within 1 degree of the target for the pure orientation test and 1 mm of the target for the pure translation test, the object changed colors to signal a match, and the subject was required to maintain the object within this threshold for 1.5 sec, at which point T was recorded and the 1.5 sec hold time was subtracted. The assigned thresholds for pose matching success, which are some-what arbitrary, were selected based on pilot tests so as to be generally attainable so that no contingencies would be required in the event that a subject was unable to complete a pose matching trial.

Figure 8A:
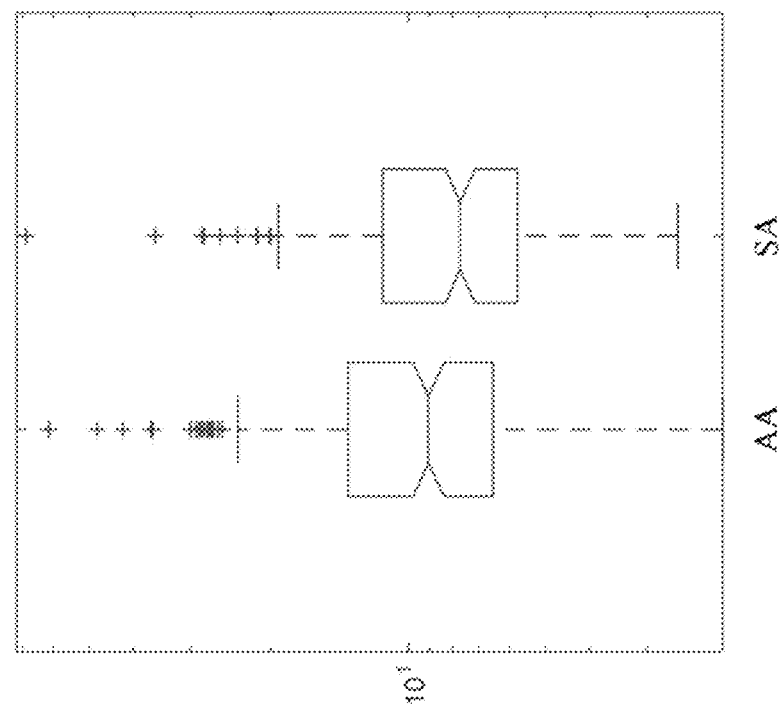
FIGS. 8a and 8b are graphs showing results for Experiment 1.
Figure 8B:
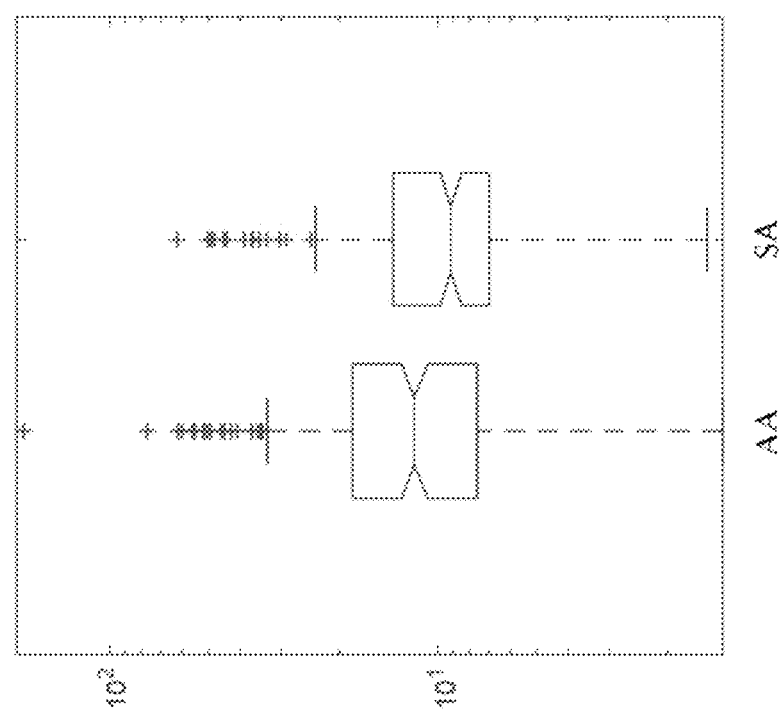

The results of Experiment 1 are presented in FIGS. 8a and 8b, wherein the graphs show for all subjects shown together, for (a) pure orientation and (b) pure translation, comparing the completion time T for AA and SA methods, shown as a notched box-whisker plot on a logarithmic scale. The red line represents the median datum, the notch represents the confidence interval of the median, the lower and upper edges of the box represent the first and third quartiles of the data, respectively, the lower/upper whiskers represent the smallest/largest datum within 1.5 IQR, and the red crosses represent outliers. The T data was skewed, and a gamma distribution was a good model for the data.

Analysis found that the SA method is faster than AA method for both pure orientations and pure translations. For pure orientations (from Session A) the median T of the AA method was 29% longer than the median T of SA method. For the pure translations (from Session B) the median T of AA method was 17% longer than the median T of SA method.

Based on these results, the SA method was used in all subsequent experiments. The SA method appears to be better than the AA method because it reduces the cognitive burden of the task by always presenting a clear unambiguous guidance command to the user, whereas the AA method ultimately requires the user to make a choice about which arrow to follow first.

Experiment 2

A human-subject study was conducted comprising four adult males and four adult females. The subjects had normal (corrected) vision and normal motor functions by self-report. None of the subjects had participated in Experiment 1.

A Polaris Spectra optical tracker was used to detect the position and orientation of the same unconstrained object as used previously in Experiment 1. A 1016 mm (40 in) LCD monitor was positioned 3.83 mm (6 ft) in front of a subject sitting at a table. The Polaris system was placed below the monitor. The height of the chair was adjusted for each subject so that they could comfortably rest their elbows on the table or the armrests of the chair.

Figure 9B:
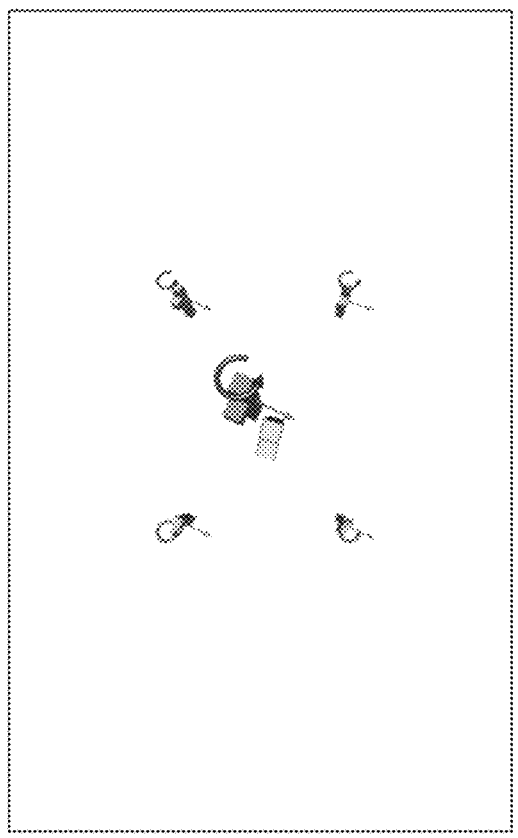
FIGS. 9a and 9b illustrate a setup for Experiment 2 comparing a triplanar display with the visual cue method.
Figure 9A:
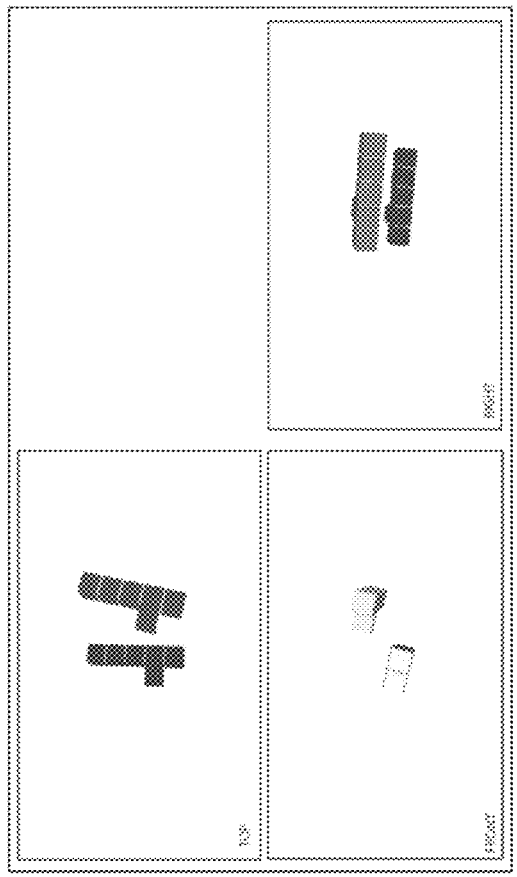

The experiment was divided into two Sessions. Session A was designed to evaluate guidance using a triplanar display. There is no standard arrangement used in prior work, so an arrangement was chosen in which a front view was positioned at the bottom left corner, a side view at the lower right, and a top view at the top left, as shown in FIG. 9a. This arrangement was consistent with common mechanical-drawing techniques. The goal in the triplanar navigation design was to make the display both as intuitive as possible to the subject, and consistent with modern practices using this technique.

Session B was designed to evaluate guidance using the visual cue method. An example screenshot is shown in FIG. 9b. The size of the objects was constrained such that the principal object view was the same size as the objects in the triplanar display. This choice was made to avoid a potential confounding factor of object size in this experiment.

The experiment used a counterbalanced approach in a repeated-measures design, examining completion time to match a virtual object, whose movement was controlled by the physical object, to a static virtual target pose using either three orthogonal views of the object or virtual arrow cues for guidance. Session A measured completion time T using the triplanar display, and Session B measured T using the visual cue method. Sessions were counterbalanced equally between male and female subjects: two male and two female subjects began with Session A and the remaining four subjects began with Session B. Each session lasted 16-61 minutes. Sessions were separated by two days to mitigate effects of learning and fatigue.

A set of 30 target poses was randomly generated for use in both sessions and by all subjects. For each pose, translational offsets were assigned along each of the three principal axes drawn from uniform distributions in the range 40 mm from the home position, and a rotational offset of 15 was assigned (using the angle-axis formulation) about an axis drawn from a uniform distribution on the sphere. The order of the 30 poses was randomized for each session and subject, in order to mitigate the effects of learning or fatigue.

A generalized linear regression analysis is used to determine statistical significance of treatment factor navigation method (treated as a fixed-effect variable) on the response completion time T, using blocking factors subject (treated as random-effect variable) and session order (treated as fixed-effect variable). The conventional significance for the entire analysis was determined at=0:05.

In each session, two virtual objects similar to the object held by the subject appeared on the monitor. One acted as a stationary target pose to be matched. The second moved as directed by the physical object guided by the subject. Subjects were instructed to move the object to the target pose as quickly as possible. For Session A, the three orthogonal views of the manipulated object in the triplanar display were explained to the subject. For Session B, subjects were instructed to perform gross alignment first, and then use the given arrow cues to perform the final alignment. Additional instructions related to avoiding camera workspace boundaries were given. Each session was preceded by a short training stage in which the subject became familiar with the method before data collection began. Each session was separated into two subsessions, and subjects were instructed to take a break between subsessions for at least 30 seconds (but longer if desired) to avoid effects of fatigue. At the start of each subsession, the subject completed two trials that were not recorded and did not count toward the 15 poses of that sub session.

At the start of each trial, the subject homed the object to a specified homing position, and then moved the object to match the target pose as quickly as possible. Homing was required before every pose to ensure that the object would not go out of range of the tracking system due to rotational or translational drift. To ease the burden of homing on the subject, the required pose matching thresholds during homing were relaxed so that homing could be accomplished quickly; this should have negligible effect on the results, due to the initial gross-alignment stage. Additionally, for each trial the initial 3-DoF position adapted to the subject's preferred location to improve ergonomics; once the 3-DoF orientation was homed, the initial position was reset to the current object location provided it was within the acceptable workspace boundaries of the experiment.

During each trial, when the object was within 5 and 3 mm of the target, the object changed colors to signal a match, and the subject was required to maintain the object within this threshold for 1.5 sec, at which point T was recorded and the 1.5 sec hold time was subtracted. The assigned thresholds for pose matching success, which are somewhat arbitrary, were selected based on pilot tests so as to be generally attainable so that no contingencies would be required in the event that a subject was unable to complete a pose matching trial.

Figure 10:
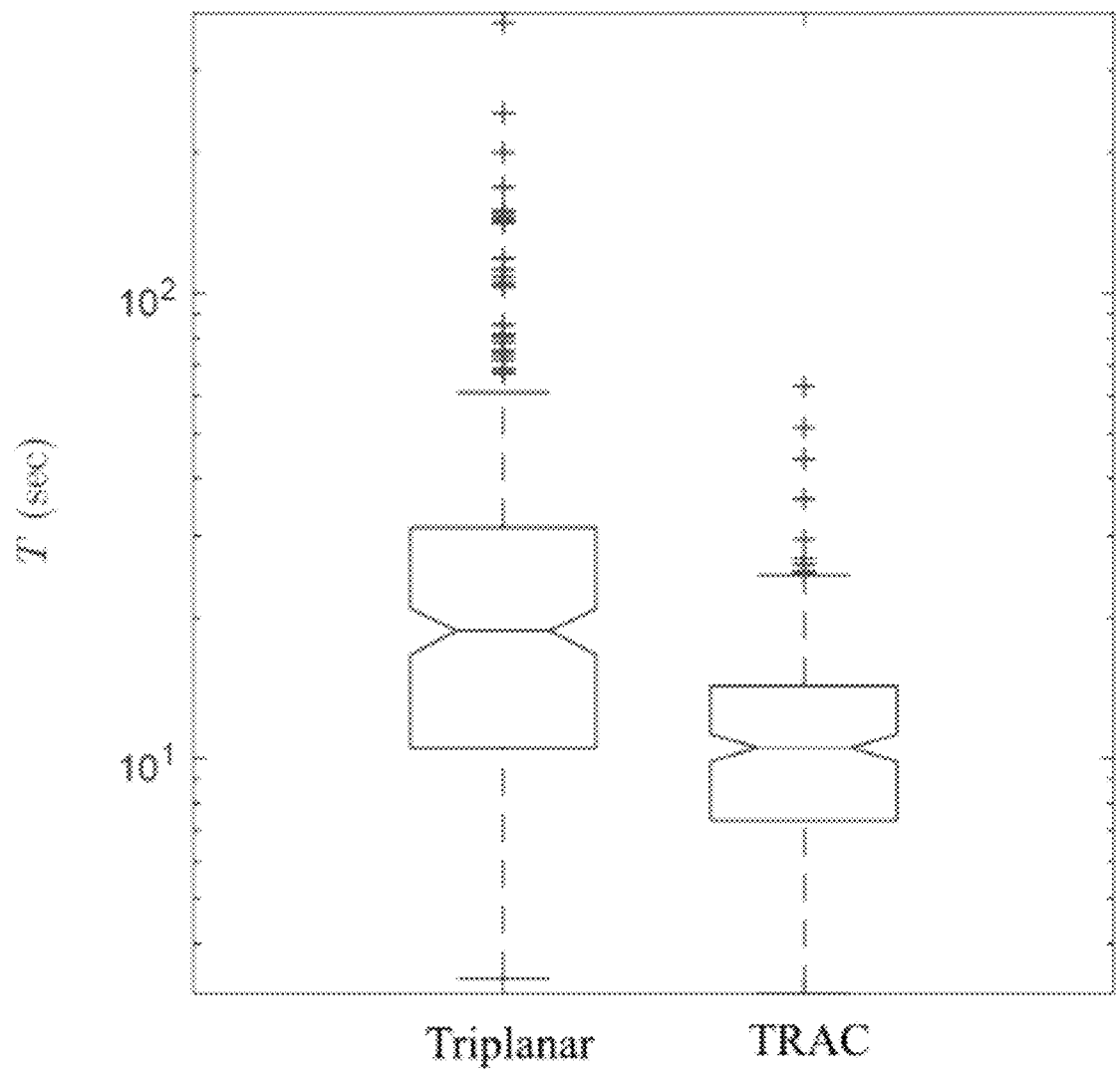
FIG. 10 is a graph showing results for Experiment 2.

The results of Experiment 2 are presented in FIG. 10. The T data was skewed, and a gamma distribution was a good model for the data. Analysis found that the visual cue method is faster than triplanar display. Using the triplanar display, the median T was 78% longer than the median T of the visual cue method. The worst-case T when using the triplanar display was more than six times longer than the worst-case T using the visual cue method. Additionally, subjects declared a unanimous preference for visual cue method.

Experiment 3

A human-subject study was conducted comprising four adult males and four adult females. The subjects had normal (corrected) vision and normal motor functions by self-report. Six of the subjects had also participated in Experiment 2.

The setup for Experiment 3 was the same as for Session A of Experiment 1. A Polaris Spectra optical tracker was used to detect the position and orientation of the same unconstrained object as used previously, which is shown in. A 483 mm (19 in) desktop monitor was positioned 3.83 m (6 ft) in front of a subject sitting at a table. The Polaris system was placed above the monitor, for tracking. The height of the chair and the placement of the haptic device were adjusted for each subject so that they could comfortably rest their elbows on the table or the armrests of the chair.

The experiment uses a counterbalanced repeated-measures design to characterize the completion time T as a function of the established accuracy thresholds when using the visual cue method to match a virtual object, whose movement was controlled by the physical object, to a static target pose. Position accuracy thresholds of 1 mm and 2 mm were tested, and orientation accuracy thresholds of 1 and 2, for a total of four position-orientation accuracy combinations.

A set of 30 target poses was randomly generated, for use by all subjects. For each pose, translational offsets were assigned at a distance of 10 mm from the home position in a direction chosen from a uniform distribution on the sphere, and a rotational offset of 15 was assigned (using the angle-axis formulation) about an axis drawn from a uniform distribution on the sphere. The four position-orientation accuracy thresholds with each of the 30 poses made up a total of 120 trials for each subject. The order of 120 trials was randomized for each subject, and split into two sessions of 60 trials separated by at least two days.

In addition to characterizing the time-accuracy trade-off with the visual cue method, a determination was made whether the subjects' performance improves with practice when using the visual cue method. A generalized linear regression analysis is used to determine statistical significance of treatment factor session number (treated as a fixed-effect variable) on the response completion time T, using blocking factors subject (treated as random-effect variable) and target pose (treated as fixed-effect variable). The conventional significance for the entire analysis was determined at=0:05.

In each session, two virtual objects similar to the object held by the subject appeared on the monitor. One acted as a stationary target pose to be matched. The second moved as directed by the physical object guided by the subject. Subjects were instructed to move the object to the target pose as quickly as possible. Subjects were instructed to perform gross alignment first, and then use the arrow cues to perform the final alignment. Additional instructions related to avoiding camera workspace boundaries were given. Each session was preceded by a short training stage in which the subject became familiar with the method before data collection began. Each session of 60 trials was separated into two subsessions of 30 trials, and subjects were instructed to take a break between subsessions for at least 30 seconds (but longer if desired) to avoid effects of fatigue. At the start of each subsession, the subject completed two trials that were not recorded and did not count toward the 30 trials of that subsession.

At the start of each trial, the subject homed the object to a specified homing position, and then moved the object to match the target pose as quickly as possible. Homing was used before every pose to ensure that the object would not go out of range of the tracking system due to rotational or translational drift. To ease the burden of homing on the subject, the required pose matching thresholds during homing were relaxed so that homing could be accomplished quickly; this should have negligible effect on the results, due to the speed of the initial gross-alignment stage. Additionally, for each trial, the initial 3-DoF position adapted to the subject's preferred location to improve ergonomics; once the 3-DoF orientation was homed, the initial position was reset to the current object location provided it was within the acceptable workspace boundaries of the experiment.

During each trial, when the object was within the specified position-orientation accuracy threshold, the object changed colors to signal a match, and the subject was required to maintain the object within this threshold for 1.5 sec, at which point T was recorded and the 1.5 sec hold time was subtracted. The object was then homed in preparation for the next target pose, as described above.

Figure 11A:
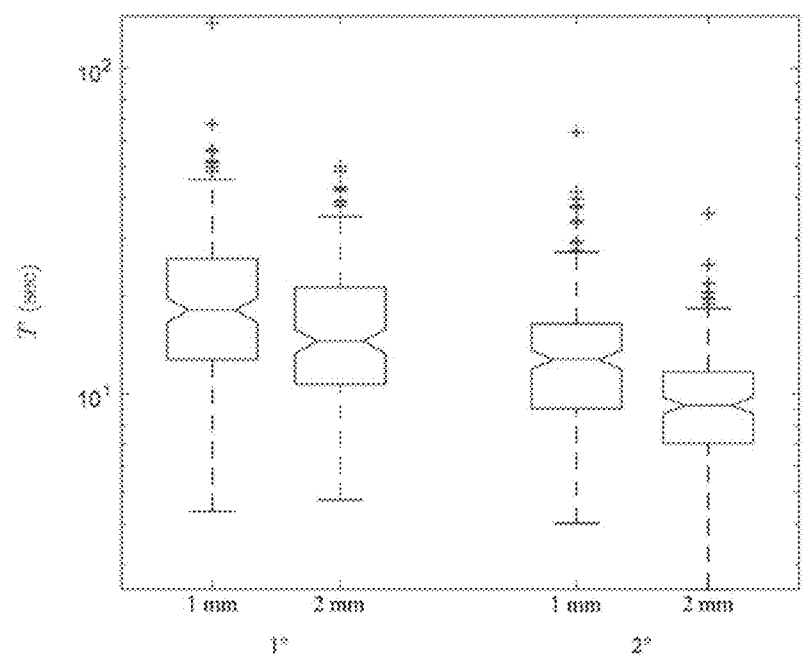
FIGS. 11a and 11b are graphs showing results for Experiment 3.

The results of Experiment 3 showing the time-accuracy trade-off are presented in FIG. 11a. The T data was skewed, and we found that a gamma distribution was a good model for the data. The median T for a position-orientation accuracy of 1 mm and 1 was 19 sec, and for a position-orientation accuracy of 2 mm and 2 it was 9 sec. That is, relaxing the accuracy thresholds both by a factor of two lead to factor-of-two improvement in completion time (with intermediate threshold combinations resulting in intermediate median completion times).

Figure 11B:
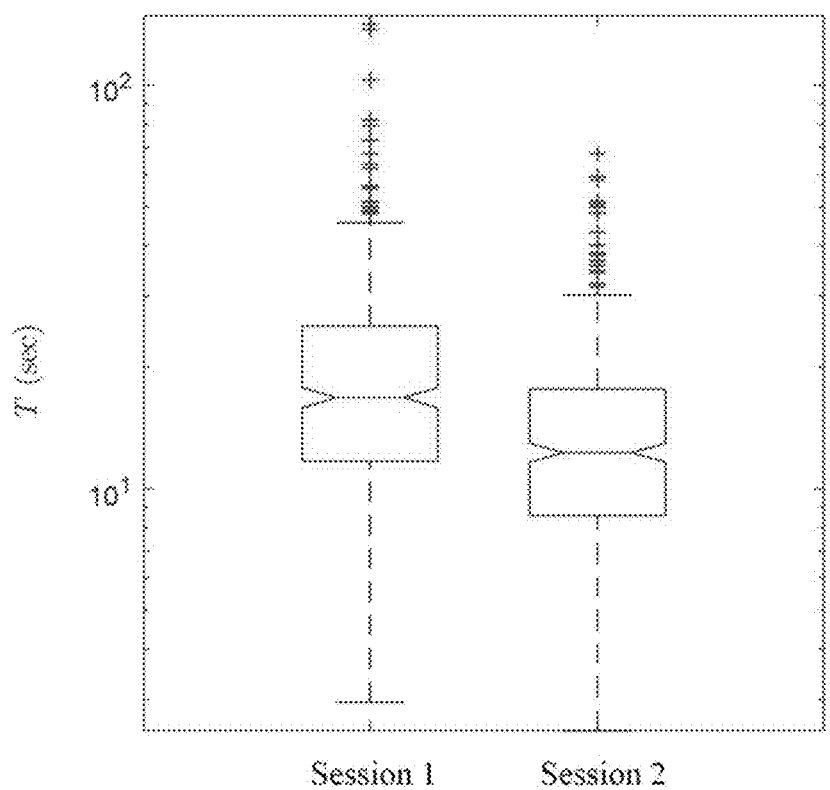

The results of Experiment 3 showing the effect of learning are presented in FIG. 11b. Statistical analysis found that subjects were significantly faster in the second session (median T of 12 sec) than in the first session (median T of 17 sec). That is, subjects' performance improves with practice using the TRAC method.

DISCUSSION

In Experiment 1, for both the pure orientation and pure translation tests, the SA method resulted in significantly faster pose alignment that the AA method, with a relatively small but non-negligible effect size. Interestingly, subjects were divided in verbal declarations of preference for the two methods. However, the results of the superiority of the SA method over the AA method are clear. It is likely that the SA method's suggestion of the best direction to move it (i.e., the direction with the largest error) enabled subjects to avoid making sub-optimal choices in which they make small corrections before first making larger orthogonal corrections. Such an effect would be most observable in orientation alignment, as orientations do not commute, and we do in fact see that the gap between the SA and AA methods is largest in the pure-orientation test.

In Experiment 2, a quite large convergence tolerance was chosen because in pilot testing many subjects struggled with completing pose alignment in a reasonable amount of time when using the triplanar display if using a tighter tolerance. Consequently, these results may underrepresent the true relative benefit of the visual cue method over the triplanar display.

In Experiment 3, an approximately inverse-proportional time-accuracy trade-off, where doubling (i.e., relaxing) the accuracy threshold by a factor of two resulted in a factor-of-two decrease in the completion time. Subjects' performance improved with increased exposure to the visual cue method. It is unclear how much practice would be required to plateau in learning, but it should certainly not be assumed the time-accuracy values reported in FIG. 11a represent the best performance that could be expected from users with training.

Finally, it should be noted that the object used throughout this study was small and light, and had three distinct visually discernible axes. It is possible that the time-accuracy trade-off, and even the achievable accuracy, will change with an increase in the object's size or mass. Gravity-compensation mechanisms may mitigate this eventuality. For objects without three distinct axes (e.g., a cube or a simple cylinder), the optical-motion-tracking rigid body can be used to disambiguate the object's axes.

What is claimed is:

1. A visual guidance system for posing a physical object within three-dimensional (3D) space, comprising:
   at least one processor;
   a memory device including instructions that, when executed by the at least one processor, cause the system to:
   receive pose data indicating a current position and orientation of the physical object within 3D space;
   calculate at least two of six degrees of freedom (6DoF) errors based on a difference between the current position and orientation of the physical object and a target pose of the physical object, wherein the at least two of the 6DoF errors are used to determine a translation direction and a rotation direction to move the physical object to align a pose of the physical object with the target pose of the physical object within a tolerance;
   output, to a display, a virtual representation of the current position and orientation of the physical object as a virtual pose indicated by the pose data; and
   output, to the display, at least one of:
      a translation cue to indicate the translation direction to move the physical object along a translation axis of the physical object to align a position of the physical object with the target pose of the physical object within the tolerance, and
      a rotation cue to indicate the rotation direction to move the physical object along a rotation axis of the physical object to align an orientation of the physical object with the target pose of the physical object within the tolerance,
   wherein the translation cue and the rotation cue are visual cues for posing the physical object to correspond to the target pose of the physical object within the tolerance, and a visual cue linked to at least one of a greater position error or orientation error as compared to other errors included in the 6DoF errors is selected for output to the display, and
   wherein one or both of:
      the instructions that, when executed by the at least one processor, cause the system to output the translation cue to the display, further: identify a greatest position error that is greater than other three degrees of freedom (3DoF) position errors; and output the translation cue linked to the greatest position error to the display, wherein output of translation cues is alternated between the translation cues based on the greatest of the 3DoF position errors; and
      the instructions that, when executed by the at least one processor, cause the system to output the rotation cue to the display, further: identify a greatest orientation error that is greater than other three degrees of freedom (3DoF) orientation errors and output the rotation cue linked to the greatest orientation error to the display, wherein output of rotation cues is alternated between the rotation cues based on the greatest of the 3DoF orientation errors.

2. The system in claim 1, wherein the virtual representation of the current position and orientation of the physical object is at least one of: a virtual object that represents the physical object, a coordinate frame that represents the physical object, or the coordinate frame attached to the virtual object.

3. The system in claim 2, wherein the translation cue is displayed as a straight arrow along the translation axis of the coordinate frame to indicate the translation direction to move the physical object.

4. The system in claim 2, wherein the rotation cue is displayed as a curved arrow along the rotation axis of the coordinate frame to indicate the rotation direction to move the physical object.

5. The system in claim 1, wherein the memory device further includes instructions that, when executed by the at least one processor, cause the system to receive the pose data from a motion tracking device which provides a data stream used to continuously update the virtual pose represented by the virtual representation.

6. The system in claim 1, wherein the memory device further includes instructions that, when executed by the at least one processor, cause the system to output a virtual representation of the target pose to the display.

7. The system in claim 1, wherein the memory device further includes instructions that, when executed by the at least one processor, cause the system to:
determine that a current pose of the physical object corresponds to the target pose of the physical object within the tolerance; and
output an indication of success that the current pose of the physical object corresponds to the target pose of the physical object.

8. The system in claim 1, wherein the at least two of the 6DoF errors include two to five errors.

9. The system in claim 1, wherein the memory device further includes instructions that, when executed by the at least one processor, cause the system to:
determine that the at least two of the 6DoF errors are within the tolerance of the target pose of the physical object; and
output an indication of success that the current pose of the physical object corresponds to the target pose of the physical object.

10. A computer implemented method, comprising:
receiving pose data from a motion tracking system indicating a current position and orientation of a physical object within 3D space, wherein the pose data provides a view of the physical object used to generate a virtual view of the physical object;
calculating at least two of six degrees of freedom (6DoF) error based on a difference between the current position of the physical object and a target pose of the physical object, wherein the 6DoF error includes a three degrees of freedom (3DoF) position error and a 3DoF orientation error that determine a translation direction and a rotation direction to move the physical object to align a pose of the physical object with the target pose of the physical object within a tolerance;
outputting a virtual object to a display to represent the physical object and the current position and orientation of the physical object as a virtual pose from the view provided by the pose data; and
outputting to the display at least one of:
a translation cue to indicate the translation direction to move the physical object along a translation axis of the physical object based on the 3DoF position error in order to align a position of the physical object with the target pose of the physical object within a position tolerance, or
a rotation cue to indicate the rotation direction to move the physical object along a rotation axis of the physical object based on the 3DoF orientation error in order to align an orientation of the physical object with the target pose of the physical object within an orientation tolerance,
wherein the translation cue and the rotation cue are visual cues for posing the physical object to correspond to the target pose of the physical object within the position tolerance and the orientation tolerance, and a visual cue linked to a greater position error or orientation error as compared to other errors in the 6DoF errors is selected for output to the display, and
wherein one or both of:
the instructions that, when executed by the at least one processor, cause the system to output the translation cue to the display, further: identify a greatest position error that is greater than other three degrees of freedom (3DoF) position errors; and output the translation cue linked to the greatest position error to the display, wherein output of translation cues is alternated between the translation cues based on the greatest of the 3DoF position errors; and
the instructions that, when executed by the at least one processor, cause the system to output the rotation cue to the display, further: identify a greatest orientation error that is greater than other three degrees of freedom (3DoF) orientation errors; and output the rotation cue linked to the greatest orientation error to the display, wherein output of rotation cues is alternated between the rotation cues based on the greatest of the 3DoF orientation errors.

11. The method in claim 10, further comprising outputting a coordinate frame that is attached to the virtual object to indicate a location of the virtual object in 3D space,
wherein the translation cue is displayed as a straight arrow along the translation axis of the coordinate frame displayed on the virtual object to indicate the translation direction to move the physical object, and the rotation cue is displayed as a curved arrow along the rotation axis of the coordinate frame displayed on the virtual object to indicate the rotation direction to move the physical object.

12. The method in claim 11, wherein the coordinate frame includes three linearly independent axes that are mutually orthogonal.

13. The method in claim 10, wherein one of the translation cue or the rotation cue is displayed until a corresponding a one degree of freedom (1DoF) error (DoF of the 3DoF position error or 1DoF of the 3DoF orientation error) is within the tolerance.

14. The method in claim 10, further comprising outputting a virtual representation of the target pose to the display to provide a visual indication of the target pose.

15. The method in claim 10, further comprising outputting to the display multiple virtual objects comprising multiple views of the physical object, wherein the multiple virtual objects are displayed with at least one of the translation cue or the rotation cue.

16. The method in claim 10, wherein the motion tracking system includes at least one of an optical motion tracker, an electromagnetic motion tracker, a kinematic linkage comprising joint sensors, or a sensor mounted on the physical object.

17. The method in claim 10, further comprising
detecting that the current position of the physical object corresponds to the target pose of the physical object within the tolerance; and
outputting an indication that the current position of the physical object corresponds to the target pose of the physical object.

18. The method in claim 10, wherein the at least two of the 6DoF errors include two to five errors.

19. The method of claim 10, wherein the at least two of the 6DoF include only five degrees of freedom (5DoF) with 3DoF position errors and two degrees of freedom (2DoF) orientation errors, or 2DoF position errors and 3DoF orientation errors.

20. A non-transitory machine readable storage medium including instructions embodied thereon, wherein the instructions, when executed by at least one processor:
receive pose data from a motion tracking system that indicates a current position and orientation of a physical object within three dimensional (3D) space, wherein the pose data provides a view of the physical object that substantially corresponds to a user view of the physical object;
calculate at least two of six degrees of freedom (6DoF) error based on a difference between the current position of the physical object and a target pose of the physical object, wherein the 6DoF error includes a three degrees of freedom (3DoF) position error and a 3DoF orientation error that determine a translation direction and a rotation direction to move the physical object to align a pose of the physical object with the target pose of the physical object within a tolerance;
output a coordinate frame to a display, wherein the coordinate frame represents a current position and orientation of the physical object in the 3D space from the user view of the physical object as indicated by the pose data;
output to the display at least one of:
a translation cue to indicate the translation direction to move the physical object along a translation axis of the physical object based on the 3DoF position error in order to align a position of the physical object with the target pose of the physical object within a tolerance, or
a rotation cue to indicate the rotation direction to move the physical object along a rotation axis of the physical object based on the 3DoF orientation error in order to align an orientation of the physical object with the target pose of the physical object within the tolerance,
wherein output of translation cues and the rotation cues to the display is iteratively updated and the translation cue and the rotation cue are visual cues for posing the physical object to correspond to the target pose of the physical object within the tolerance, and a visual cue linked to a greater position error or orientation error as compared to other errors in the 6DoF errors is selected for output to the display; and
output an indication of success when the current position and orientation of the physical object corresponds to the target pose of the physical object,
wherein the instructions, when executed by the at least one processor, further:
output to the display the rotation cue for each rotational axis of the physical object, wherein output of the rotation cue is alternated between each rotational axis until an orientation error is within the tolerance of the target pose; and
output to the display the translation cue for each translation axis of the physical object, wherein output of the translation cue is alternated between each translation axis until a position error is within the tolerance of the target pose.

21. The non-transitory machine readable storage medium in claim 20, further comprising instructions, that when executed by the at least one processor, output a virtual object to the display to represent the physical object and the current position and orientation of the physical object as indicated by the pose data, wherein the virtual object is output to overlay the coordinate frame.

22. The non-transitory machine readable storage medium in claim 20, wherein the translation cue is animated to indicate the translation direction, and the rotation cue is animated to indicate the rotation direction.

* * * * *